United States Patent
Strongin et al.

(10) Patent No.: US 9,229,007 B2
(45) Date of Patent: Jan. 5, 2016

(54) FLUORESCENCE DETECTION OF CYSTEINE AND HOMOCYSTEINE

(75) Inventors: Robert Strongin, Portland, OR (US); Xiaofeng Yang, Xi'an (CN)

(73) Assignee: Portland State University, Portland, OR (US)

( * ) Notice: Subject to any disclaimer, the term of this patent is extended or adjusted under 35 U.S.C. 154(b) by 45 days.

(21) Appl. No.: 14/236,791

(22) PCT Filed: Aug. 2, 2012

(86) PCT No.: PCT/US2012/049379
§ 371 (c)(1),
(2), (4) Date: Mar. 28, 2014

(87) PCT Pub. No.: WO2013/019978
PCT Pub. Date: Feb. 7, 2013

(65) Prior Publication Data
US 2014/0206095 A1 Jul. 24, 2014

Related U.S. Application Data

(60) Provisional application No. 61/514,697, filed on Aug. 3, 2011.

(51) Int. Cl.
*G01N 33/68* (2006.01)
*G01N 33/50* (2006.01)
*G01N 33/00* (2006.01)
*C07D 277/66* (2006.01)

(52) U.S. Cl.
CPC .............. *G01N 33/68* (2013.01); *C07D 277/66* (2013.01); *G01N 33/6815* (2013.01); *Y10T 436/17* (2015.01); *Y10T 436/173845* (2015.01)

(58) Field of Classification Search
CPC ... G01N 33/68; G01N 33/6815; G01N 33/50; G01N 33/48; G01N 33/00; Y10T 436/173845; Y10T 436/17; Y10T 436/00
USPC .............................. 436/111, 106; 422/430, 50
See application file for complete search history.

(56) References Cited

FOREIGN PATENT DOCUMENTS

| | | |
|---|---|---|
| JP | 2005/302641 | 10/2005 |
| JP | 2010/215693 | 9/2010 |
| WO | WO 91/01128 A1 | 2/1991 |
| WO | WO 91/01301 A1 | 2/1991 |
| WO | WO 03/053368 A2 | 7/2003 |
| WO | WO 2010/024463 A1 | 3/2010 |

OTHER PUBLICATIONS

Blondeau et al., "Synthesis of Some Stable 7-Halo-1,4-thiazepines. Potential Substituted Penam Precursors," *Can. J. Chem.*, 49:3866-3876 (1971).
CAS RN 868248-18-4, STN Entry Date Nov. 17, 2005.
CAS RN 902085-40-9, STN Entry Date Aug. 17, 2006.
CAS RN 902085-02-3, STN Entry Date Aug. 17, 2006.
CAS RN 1246026-50-5, STN Entry Date Oct. 12, 2010.
Chen et al., "In-vivo Activity of Retinoid Esters in Skin is Related to In-vitro Hydrolysis Rate," *Journal of Pharmacy and Pharmacology*, 47(8):626-631 (1995).
Hashimoto et al., "Ru/Ag-Catalyzed Oxidative Alkenylation of Benzamides and Phenylazoles through Regioselective C—H Bond Cleavage," *Chemistry Letters*, 41(2):151-153 (2012).
International Search Report and Written Opinion issued Sep. 7, 2012, by the Australian Patent Office, for corresponding Application No. PCT/US2012/049379 (13 pages).
Khatik et al., "Catalyst-Free Conjugated Addition of Thiols to α,β-Unsaturated Carbonyl Compounds in Water, " *Org. Lett.*, 8:2433-2436 (2006).
Leonard et al., "The Synthesis and Stereochemistry of Substituted 1,4-Thiazepines Related to the Penicillins," *J. Org. Chem.*, 31:3928-3935 (1966).
Lochbrunner et al., "Ultrafast excited-state proton transfer and subsequent coherent skeletal motion of 2-(2'-hydroxypheny)benzothiazole," *J. Chem. Phys.* 112:10699-10702 (2000).
Sharma et al., "'On water' synthesis of 2,4-diaryl-2,3-dihydro-1,5-benzothiazepines catalysed by sodium dodecyl sulfate (SDS)," *Tetrahedron Lett.*, 49:4269-4271, 2008.
Yang, X, et al., "Conjugate Addition/Cyclization Sequence Enables Selective and Simultaneous Fluorescence Detection of Cysteine and Homocysteine,"*Angewandte Chemie*, International edition in English, 50(45):10690-10693 (2011).

*Primary Examiner* — Christine T Mui
(74) *Attorney, Agent, or Firm* — Klarquist Sparkman, LLP

(57) ABSTRACT

Embodiments of probes for selectively detecting compounds having a thiol group and an amino group, e.g., cysteine and/or homocysteine, are disclosed, along with methods and kits for detecting the compounds in neutral media with the probes. The probes have a structure according to the general formula where $R^1$-$R^4$ independently are hydrogen hydroxyl, halogen, thiol, thioether, lower aliphatic, or lower alkoxy, x is an integer from 0 to 4, and each $R^5$ independently is halogen, hydroxyl, thiol, thioether, lower aliphatic, or lower alkoxy. Embodiments of the disclosed probes are capable of undergoing condensation/cyclization reactions with cysteine and/or homocysteine. Cysteine and/or homocysteine can be selectively detected and identified by determining fluorescence emission of the probes at characteristic wavelengths.

14 Claims, 33 Drawing Sheets

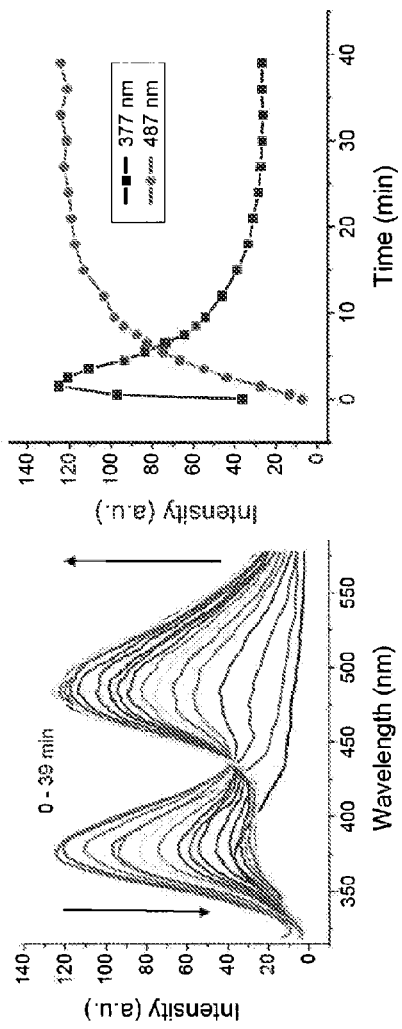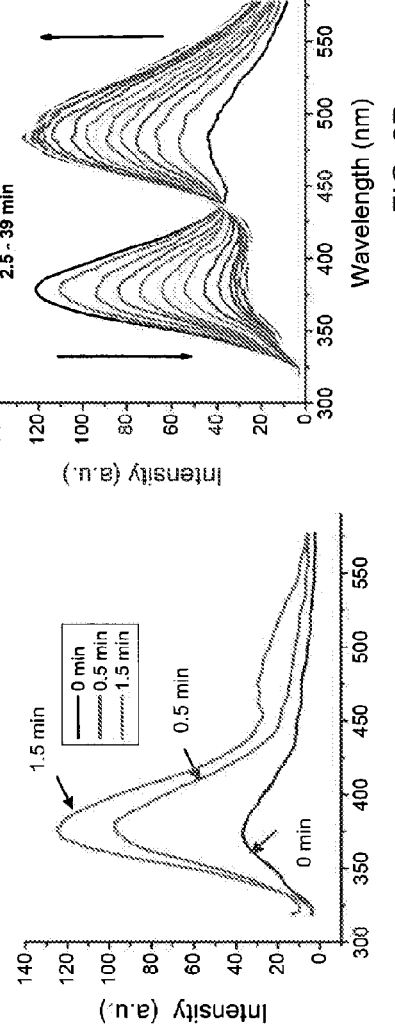

FLUORESCENCE DETECTION OF CYSTEINE AND HOMOCYSTEINE

ACKNOWLEDGMENT OF GOVERNMENT SUPPORT

This invention was made with government support under Award RO1 EB002044 awarded by National Institutes of Health. The government has certain rights in the invention.

CROSS REFERENCE TO RELATED APPLICATIONS

This application is the U.S. National Stage of International Application No. PCT/US2012/049379, filed Aug. 2, 2012, which was published in English under PCT Article 21(2), which in turn claims the benefit of U.S. Provisional Application No. 61/514,697, filed Aug. 3, 2011, each of which is incorporated by reference in its entirety.

FIELD

Embodiments of fluorescent probes capable of selectively detecting cysteine and homocysteine simultaneously in neutral media are disclosed.

BACKGROUND

Biological thiols are essential in maintaining the appropriate redox status of proteins, cells and organisms (Wood et al., *Trends Biochem. Sci.* 2003, 28, 32-40; Schultz et al., *Eur. J. Biochem.* 2000, 267, 4904-4911). Cysteine (Cys) is an essential amino acid that is involved in protein synthesis, detoxification, and metabolism. Elevated levels of Cys have been associated with neurotoxicity (Wang et al., *J. Neurosci.* 2001, 21, 3322-3331). Cys deficiency is involved in slowed growth, hair depigmentation, edema, lethargy, liver damage, muscle and fat loss, skin lesions, and weakness (Shahrokhian, *Anal. Chem.* 2001, 73, 5972-5978). Homocysteine (Hcy) has been implicated in various types of vascular and renal diseases. Elevated Hcy (e.g., >12 µM) in blood is a well-known risk factor for cardiovascular, Alzheimer's disease, neutral tube defects, complications during pregnancy, inflammatory bowel disease, and osteoporosis (Seshadri et al., *N. Eng. J. Med.* 2002, 346, 476-483; Refsum et al., *Annu. Rev. Med.* 1998, 49, 31-62). Therefore, the determination of Cys and Hcy in vivo is correlated to physiological functions in diagnosing disease. However, because Cys and Hcy levels are associated with different diseases despite their similar structures, a need exists for a method to discriminate between Cys and Hcy.

Significant effort has gone into the development of colorimetric, phosphorescent, and fluorescent probes for these thiol-containing amino acids to achieve high sensitivity, low cost and ease of detection. To date, most of the indicators or dosimeters are based on the strong nucleophilicity of the thiol group, and various mechanisms have been employed, including Michael addition, cleavage reactions, and others. Though these probes show high sensitivity toward thiol-containing compounds, the direct detection of Cys (or Hcy) is hampered due to interference from other thiols.

For example, Cys and Hcy are known to undergo cyclization with aldehydes to form thiazolidines (or thiazinanes). Because both the sulfhydryl and the amino groups contribute to the cyclization, aldehyde cyclization enables selectivity for Cys and Hcy over other common thiols such as glutathione (GSH). However, since the aminothiol moieties of Cys and Hcy have similar reactivities towards aldehydes in general, discrimination of them from each other is challenging using heterocycle formation (Li et al., *Chem. Comm.* 2009, 5904-5906; Lee et al., *Chem. Commun.* 2008, 6173-6175; Tanaka et al., *Chem. Commun.* 2004, 1762-1763; Li et al., *Chem. Commun.* 2009, 5904-5906; Duan et al., *Tetrahedron Lett.* 2008, 49, 6624-6627; Kim et al., *Tetrahedron Lett.* 2008, 49, 4879-4881; Zhang et al., *Tetrahedron Lett.* 2007, 48, 2329-2333; Zhang et al., *Org. Lett.* 2009, 11, 1257-1260; Lim et al., *Chem. Commun.* 2010, 46, 5707-5709).

SUMMARY

Embodiments of probes capable of selectively detecting thiol-containing compounds are disclosed. Embodiments of methods for using the probes and kits including the probes also are disclosed.

Some embodiments of the disclosed probe include a fluorophore moiety having a chemical structure according to formula I

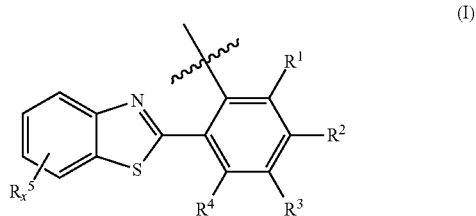

where $R^1$-$R^4$ independently are hydrogen, hydroxyl, halogen, thiol, thioether, lower aliphatic, or lower alkoxy, x is an integer from 0 to 4, and each $R^5$ independently is halogen, hydroxyl, thiol, thioether, lower aliphatic, or lower alkoxy, and an α,β-unsaturated carbonyl moiety. In certain embodiments, $R^1$ is methoxy. In particular embodiments, $R^1$ is methoxy, $R^2$-$R^4$ are hydrogen, and x is 0. In some embodiments, the α,β-unsaturated carbonyl moiety is an acrylate ester.

In certain embodiments, the probe has a chemical structure according to general formula II

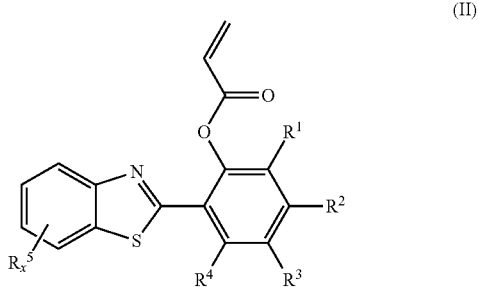

where $R^1$-$R^4$ independently are hydrogen, hydroxyl, halogen, thiol, thioether, lower aliphatic, or lower alkoxy, x is an integer from 0 to 4, and each $R^5$ independently is halogen, hydroxyl, thiol, thioether, lower aliphatic, or lower alkoxy. In some embodiments, $R^1$ is methoxy. In particular embodiments, $R^1$ is methoxy, $R^2$-$R^4$ are hydrogen, and x is zero.

Some embodiments of the disclosed probes are capable of undergoing a condensation/cyclization reaction with a compound comprising a thiol group and an amino group. Certain embodiments of the disclosed probes produce a fluorescence spectrum having an emission spectrum maximum at a first wavelength after condensation with the compound, and subsequently produce a fluorescence spectrum having an emission spectrum maximum at a second wavelength after cyclization, wherein the first and second wavelengths are different from one another. In particular embodiments, the probes are capable of undergoing condensation/cyclization reactions with cysteine and/or homocysteine.

Embodiments of a method for detecting at least one compound having a thiol group and an amino group include combining a sample potentially comprising at least one compound comprising a thiol group and an amino group with a solution comprising a probe having a structure according to general formula II, allowing a reaction between the compound and the probe to proceed for an effective period of time, and detecting the at least one compound by detecting fluorescence of the solution. In certain embodiments, the solution has a pH of 7-8. In some embodiments, the compound is cysteine, homocysteine, or a combination thereof.

In some embodiments, fluorescence of the solution is detected by obtaining a fluorescence spectrum after the effective period of time. In certain embodiments, a fluorescence spectrum of the solution is monitored over a period of time ranging from zero minutes to a time greater than or equal to the effective period of time.

In some embodiments, when $R^1$ in general formula II is methoxy, $R^2$ is hydrogen, and x is 0, fluorescence is detected at 377 nm, at 487 nm, or at 377 nm and 487 nm after the effective period of time. In certain embodiments, fluorescence is detected at 377 nm, at 487 nm, or at 377 nm and 487 nm over a period of time ranging from zero minutes to the effective period of time.

In embodiments where the at least one compound is cysteine, fluorescence of the solution can be detected at 487 nm after the effective period of time, e.g., after at least 5 minutes, such as after 5-60 minutes. In embodiments where the at least one compound is homocysteine, fluorescence of the solution can be detected at 377 nm after the effective period of time, e.g., after 5-60 minutes.

In some embodiments, the probe solution further includes a surfactant. In certain embodiments, the surfactant is cetyltrimethylammonium bromide. When a surfactant is included, the effective period of time may be at least 5 minutes, e.g., 8-10 minutes when $R^1$ in general formula II is methoxy, $R^2$ is hydrogen, and x is 0. In such embodiments, when the at least one compound is cysteine, fluorescence of the solution can be detected at 487 nm after the effective period of time. In some embodiments when the at least one compound is homocysteine, fluorescence of the solution can be detected at 377 nm 8-10 minutes after combining the sample and the solution comprising the probe. In other embodiments when the at least one compound is homocysteine, detecting the homocysteine includes measuring fluorescence of the solution at 377 nm and 487 nm at a first time 8-10 minutes after combining the sample and the solution comprising the probe, measuring fluorescence of the solution at 377 nm and 487 nm at a second time after combining the sample and the solution comprising the probe, wherein the second time is greater than 8-10 minutes, and determining a difference in fluorescence at each of 377 nm and 487 nm at the first time and the second time, wherein a decrease in fluorescence at 377 nm and a proportional increase in fluorescence at 487 nm indicates presence of homocysteine.

In some embodiments, the at least one compound may be cysteine, homocysteine, glutathione, one or more non-amino thiols, or a combination of any two or more thereof. In such embodiments when the probe has a formula according to general formula II where $R^1$ is methoxy, $R^2$-$R^4$ are hydrogen, x is 0, and the probe solution includes a surfactant, the effective period of time may be greater than or equal to 9 minutes, and the at least one compound is detected by detecting fluorescence of the solution at 377 nm and 487 nm after the effective period of time. In some embodiments, the at least one compound is further identified. Cysteine can be identified based upon stable fluorescence of the solution at 487 nm after 9 minutes and for a subsequent period of time of at least 5 additional minutes, glutathione and/or non-amino thiols can be identified based upon stable fluorescence of the solution at 377 nm after 9 minutes and for a subsequent period of time of at least 5 additional minutes, and homocysteine can be identified based upon proportionally decreasing fluorescence of the solution at 377 nm and increasing fluorescence of the solution at 487 nm after 9 minutes and during a subsequent period of time of at least 5 additional minutes.

Embodiments of kits for detecting at least one compound comprising a thiol group and an amino group (e.g., cysteine, homocysteine, or a combination thereof) include at least one probe according to general formula II. In some embodiments, the kit further includes a buffer solution at physiologic pH, such as a phosphate solution at pH 7-8. In certain embodiments, the buffer solution also includes a surfactant, e.g., cetyltrimethylammonium bromide. Embodiments of the kits may further include a plurality of disposable containers in which a reaction between the probe and the at least one compound can be performed. In certain embodiments, an amount of the probe effective to undergo a detectable change in the probe's fluorescence emission spectrum when reacted with the at least one compound is premeasured into the plurality of disposable containers.

The foregoing and other objects, features, and advantages of the invention will become more apparent from the following detailed description, which proceeds with reference to the accompanying figures.

BRIEF DESCRIPTION OF THE DRAWINGS

FIGS. 8A-D are graphs of absorbance intensity versus wavelength (8A, 8C, 8D) or time (10B) illustrating the time-dependent fluorescence spectral changes of probe 4 (20 μM) with cysteamine (1 equiv) in EtOH:phosphate buffer (20 mM, pH 7.4, 2:8 v/v). $\lambda_{ex}$=304 nm. FIG. 8A illustrates the spectral changes at 0-39 min; FIG. 8B illustrates the time-dependent fluorescence intensity changes at 377 and 487 nm, respectively; FIG. 8C illustrates the changes in fluorescence at 0-1.5 min; FIG. 8D illustrates the changes in fluorescence at 2.5-39 min.

DETAILED DESCRIPTION

Figure 1:
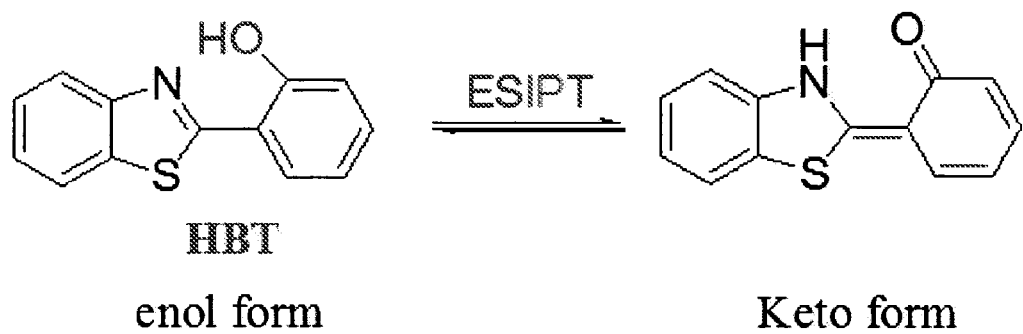
FIG. 1 illustrates the enol-keto tautomerism of 2-(2'-hydroxyphenyl)-benzothiazole.

Simultaneous determination of cysteine (Cys) and/or homocysteine (Hcy) via a single probe remains a significant challenge due to the structural similarity of Cys and Hcy which differ by a single methylene unit in their side chains.

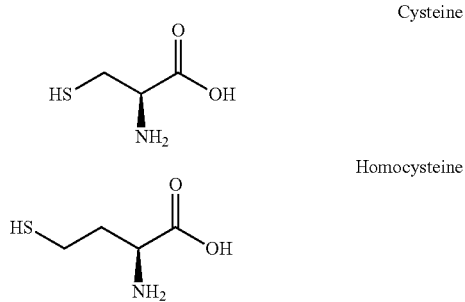

Disclosed herein are embodiments of probes that can differentiate between Cys and Hcy at physiologic pH based on their relatively different intramolecular cyclization rates. Embodiments of the disclosed probes also can discriminate Cys and Hcy from other amino acids and thiols at physiologic pH. Embodiments of the disclosed probes include a fluorophore moiety to facilitate detection and a moiety capable of undergoing a condensation-cyclization reaction (referred to as a "cyclization moiety") with Cys and/or Hcy. In some embodiments, the cyclization moiety is an α,β-unsaturated carbonyl moiety, which is covalently bonded to the fluorophore moiety.

I. TERMS AND DEFINITIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2).

In order to facilitate review of the various embodiments of the disclosure, the following explanations of specific terms are provided:

Absorbance: The retention by a compound or substance of certain wavelengths of radiation incident upon it; a measure of the amount of light at a particular wavelength absorbed as the light passes through a compound or substance, or through a solution of a compound or substance.

Aliphatic refers to a substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic groups can either be unsubstituted or substituted. An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group). Exemplary aliphatic substituents include, for instance, amine, amide, sulfonamide, halogen, cyano, carboxy, hydroxy, mercapto, trifluoromethyl, alkyl, alkoxy, alkylthio, thioalkoxy, arylalkyl, heteroaryl, alkylamino, dialkylamino, or other functionality.

Alkyl refers to a hydrocarbon group having a saturated carbon chain. The chain may be branched or unbranched. The term lower alkyl means the chain includes 1-10 carbon atoms.

Alkoxy refers to a functional group having the formula —OR where R is an alkyl group. The term lower alkoxy means that the alkyl group includes 1-10 carbon atoms.

An analogue or derivative is a compound that is derived from a similar compound, or a compound that can be imagined to arise from another compound, for example, if one atom is replaced with another atom or group of atoms. Analogues may differ from one another in one or more atoms, functional groups, or substructures, which are replaced with other atoms, groups, or substructures.

Aromatic or aryl compounds typically are unsaturated, cyclic hydrocarbons having alternate single and double bonds. Benzene, a 6-carbon ring containing three double bonds, is a typical aromatic compound.

Cyclization moiety: As used herein, the term "cyclization moiety" refers to a portion of a molecule capable of undergoing a condensation-cyclization reaction with a target compound, such as a compound comprising a thiol group and an amino group.

Detect: To determine if an agent (such as a target molecule) is present or absent, for example, in a sample. "Detecting" refers to any method of determining if something exists, or does not exist, such as determining if a target molecule is present in a biological sample. For example, "detecting" can include using a visual or a mechanical device to determine if a sample displays a specific characteristic.

Effective period of time: As defined herein, an effective period of time is a sufficient amount of time to allow a chemical reaction to occur. With respect to the present disclosure, an effective period of time is an amount of time sufficient to allow condensation of a thiol-containing compound with an embodiment of the disclosed probes and/or subsequent cyclization of the thiol-containing compound to occur.

Emission or emission signal: The light of a particular wavelength generated from a source. In particular examples, an emission signal is emitted from a fluorophore after the fluorophore absorbs light at its excitation wavelength(s).

Fluorescence is the emission of visible radiation by an atom or molecule passing from a higher to a lower electronic state, wherein the time interval between absorption and emission of energy is $10^{-8}$ to $10^{-3}$ second. Fluorescence occurs when the atom or molecule absorbs energy from an excitation source (e.g., an ultraviolet lamp) and then emits the energy as visible radiation. The term "stable fluorescence intensity" refers to a fluorescence intensity that remains substantially the same over a period of time. Substantially the same means that the fluorescence intensity changes by less than 20%, less than 15%, less than 10%, less than 5%, or less than 2% over a defined period of time.

A fluorophore, or fluorogen, is a compound capable of fluorescence, such as a fluorescent dye. The term "fluorophore" also refers to the portion of a molecule that causes the molecule to fluoresce when exposed to an excitation source.

A functional group is a specific group of atoms within a molecule that is responsible for the characteristic chemical reactions of the molecule. Exemplary functional groups include, without limitation, alkane, alkene, alkyne, arene, halo (fluoro, chloro, bromo, iodo), epoxide, hydroxyl, carbonyl (ketone), aldehyde, carbonate ester, carboxylate, ether, ester, peroxy, hydroperoxy, carboxamide, amine (primary, secondary, tertiary), ammonium, imide, azide, cyanate, isocyanate, thiocyanate, nitrate, nitrite, nitrile, nitroalkane, nitroso, pyridyl, phosphate, sulfonyl, sulfide, thiol (sulfhydryl), disulfide.

Heteroaryl compounds are aromatic compounds having at least one heteroatom, i.e., one or more carbon atoms in the ring has been replaced with an atom having at least one lone pair of electrons, typically nitrogen, oxygen, or sulfur.

An isoemissive point is a wavelength, wavenumber, or frequency at which the total intensity of emission of light by a sample does not change during a chemical reaction of physical change.

As used herein, the term "probe" refers to a molecule capable of selectively reacting with a molecule of interest (i.e., a molecule for which the presence and/or concentration is to be determined) and producing a detectable signal or change as a result of the reaction. A detectable signal or change may include a change in the absorbance spectrum and/or emission spectrum of the probe and/or the molecule of interest.

A substituent is an atom or group of atoms that replaces another atom in a molecule as the result of a reaction. The term "substituent" typically refers to an atom or group of atoms that replaces a hydrogen atom on a parent hydrocarbon chain or ring.

Substituted: A fundamental compound, such as an aryl or aliphatic compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a long-chain hydrocarbon may have a substituent bonded thereto, such as one or more halogens, an aryl group, a cyclic group, a heteroaryl group or a heterocyclic group.

Surfactant: A compound that reduces surface tension when dissolved in water or aqueous solutions. Surfactants typically are amphiphilic organic compounds, i.e., organic compounds that contain both hydrophobic groups and hydrophilic groups. Surfactants may be characterized by their hydrophilic groups, or heads. A non-ionic surfactant includes no formal charge in its head. Ionic surfactants include hydrophilic groups having a net charge. If the charge is negative, the surfactant is an anionic surfactant. If the charge is positive, it is a cationic surfactant. If the head contains two oppositely charged groups, it is a zwitterionic surfactant.

II. OVERVIEW OF REPRESENTATIVE EMBODIMENTS

Embodiments of probes that can differentiate between cysteine and homocysteine at physiologic pH are disclosed. Also disclosed are embodiments of methods and kits for performing the detection.

Embodiments of the disclosed probes include (a) a fluorophore moiety having a chemical structure according to formula I

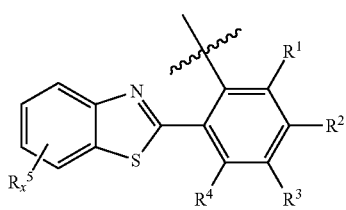

(I)

where $R^1$-$R^4$ independently are hydrogen, hydroxyl, halogen, thiol, thioether, lower aliphatic, or lower alkoxy, x is an integer from 0 to 4, and each $R^5$ independently is halogen, hydroxyl, thiol, thioether, lower aliphatic, or lower alkoxy; and (b) an α,β-unsaturated carbonyl moiety. In one embodiment, $R^1$ is methoxy. In another embodiment, $R^1$ is methoxy, $R^2$-$R^4$ are hydrogen, and x is 0. In any or all of the above embodiments, the α,β-unsaturated carbonyl moiety may be an acrylate ester.

In some embodiments, the probe has a chemical structure according to formula II

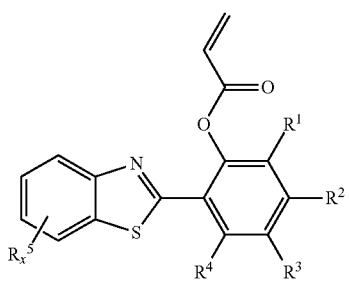

(II)

where $R^1$-$R^4$ and x are as defined above. In one embodiment, $R^1$ is methoxy. In another embodiment, $R^1$ is methoxy, $R^2$-$R^4$ are hydrogen, and x is 0.

In any or all of the above embodiments, the probe may be capable of undergoing a condensation/cyclization reaction with a compound comprising a thiol group and an amino group. In some embodiments, the probe has a first fluorescence spectrum having an emission spectrum maximum at a first wavelength after condensation with the compound, and the probe has a subsequent fluorescence spectrum having an emission spectrum maximum at a second wavelength after cyclization, wherein the first and second wavelengths are different from one another. In any or all of the above embodiments, the compound may be cysteine, homocysteine, or a combination thereof.

Embodiments of a method for detecting at least one compound comprising a thiol group and an amino group include combining a sample potentially comprising at least one compound comprising a thiol group and an amino group with a solution comprising a probe having a structure according to general formula II, allowing a reaction between the compound and the probe to proceed for an effective period of time, and detecting the at least one compound by detecting fluorescence of the solution. In some embodiments, the solution has a pH of 7-8. In any or all of the above embodiments, the at least one compound may be cysteine, homocysteine, or a combination thereof.

In any or all of the above embodiments, fluorescence of the solution may be detected by obtaining a fluorescence spectrum after the effective period of time, or by monitoring a fluorescence spectrum of the solution over a period of time ranging from zero minutes to a time greater than or equal to the effective period of time.

In any or all of the above embodiments, the probe may have a structure according to general formula II where $R^1$ is methoxy, $R^2$-$R^4$ are hydrogen, and x is 0. In one such embodiment, detecting fluorescence of the solution includes detecting the fluorescence at 377 nm, at 487 nm, or at 377 nm and 487 nm after the effective period of time. In another such embodiment, detecting fluorescence of the solution includes detecting the fluorescence at 377 nm, at 487 nm, or at 377 nm and 487 nm over a period of time ranging from zero minutes to the effective period of time. In some embodiments, the at least one compound is cysteine and detecting the at least one compound comprises detecting fluorescence of the solution at 487 nm after the effective period of time; the effective period of time may be at least 5 minutes, such as 5-60 minutes. In other embodiments, the at least one compound is homocysteine and detecting the at least one compound comprises detecting fluorescence of the solution at 377 nm after the effective period of time; the effective period of time may be 5-60 minutes.

In any or all of the above embodiments, the solution may further include a surfactant. The surfactant may be cetyltrimethylammonium bromide. In some embodiments, the effective period of time is at least 5 minutes. In some embodiments, the probe has a structure according to general formula II where $R^1$ is methoxy, $R^2$ is hydrogen, and x is 0. In such embodiments, the effective period of time may be 8-10 minutes. In one embodiment, the at least one compound is cysteine, and detecting the cysteine includes detecting fluorescence of the solution at 487 nm after the effective period of time. In another embodiment, the at least one compound is homocysteine, and detecting the homocysteine includes detecting fluorescence of the solution at 377 nm 8-10 minutes after combining the sample and the solution comprising the probe. In still another embodiment, the at least one compound is homocysteine, and detecting the homocysteine includes (1) measuring fluorescence of the solution at 377 nm and 487 nm at a first time 8-10 minutes after combining the sample and the solution comprising the probe; (2) measuring fluorescence of the solution at 377 nm and 487 nm at a second time after combining the sample and the solution comprising the probe, wherein the second time is greater than 8-10 minutes; and (3) determining a difference in fluorescence at each of 377 nm and 487 nm at the first time and the second time, wherein a decrease in fluorescence at 377 nm and a proportional increase in fluorescence at 487 nm indicates presence of homocysteine. In yet another embodiment, the at least one compound comprises cysteine, homocysteine, glutathione, one or more non-amino thiols, or a combination thereof, the effective period of time is greater than or equal to 9 minutes, and detecting the at least one compound comprises detecting fluorescence of the solution at 377 nm and 487 nm after the effective period of time. The method may further include identifying the at least one compound, wherein cysteine is identified based upon stable fluorescence intensity of the solution at 487 nm after 9 minutes and for a subsequent period of time of at least 5 additional minutes, glutathione and/or non-amino thiols are identified based upon stable fluorescence intensity of the solution at 377 nm after 9 minutes and for a subsequent period of time of at least 5 additional minutes, and/or homocysteine is identified based upon proportionally decreasing fluorescence intensity of the solution at 377 nm and increasing fluorescence intensity of the solution at 487 nm after 9 minutes and during a subsequent period of time of at least 5 additional minutes.

Embodiments of a kit for detecting at least one compound comprising a thiol group and an amino group include at least one probe according to general formula II. The at least one compound may be cysteine, homocysteine, or a combination thereof. In any or all of the above embodiments, the kit may further include a buffer solution at physiologic pH. In some embodiments, the buffer solution is a phosphate solution at pH 7-8. The buffer solution may further include a surfactant, such as cetyltrimethylammonium bromide. In any or all of the above embodiments, the kit may also include a plurality of disposable containers in which a reaction between the probe and the at least one compound can be performed. In some embodiments, an amount of the probe effective to undergo a detectable change in the probe's fluorescence emission spectrum when reacted with the at least one compound is premeasured into the plurality of disposable containers.

III. OVERVIEW OF CONJUGATE ADDITION-CYCLIZATION

Cysteine (Cys) and homocysteine (Hcy) are structurally related, differing in the presence of a single extra methylene group in the side chain of Hcy. Cysteine is capable of undergoing condensation with acrylates to form substituted 1,4-thiazepines (Blondeau et al., *Can. J. Chem.* 1971, 49, 3866-3876; Leonard et al., *J. Org. Chem.* 1966, 31, 3928-3935). The reaction involves the conjugate addition of Cys to acrylates (1) to generate thioether (2), which can further undergo an intramolecular cyclization to yield the desired compound 3a (3-carboxy-5-oxoperhydro-1,4-thiazepine), as illustrated in Scheme 1.

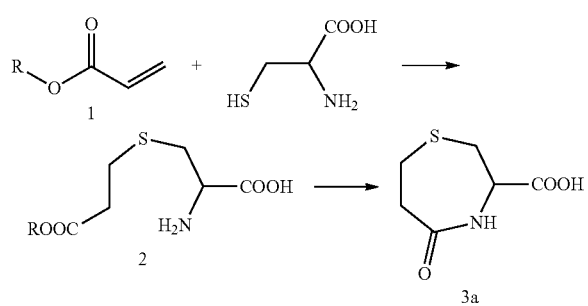

An analogous thioether can be generated from Hcy (Khatik, *Org. Lett.* 2006, 8, 2433-2436). However, the intramolecular cyclization reaction to form an eight-membered ring is kinetically disfavored relative to the seven-membered ring as in the case of Cys, i.e., homocysteine's cyclization rate is expected to be less than cysteine's cyclization rate.

IV. PROBES

Embodiments of the disclosed probes include a fluorophore moiety and a cyclization moiety capable of undergoing a condensation-cyclization reaction with a compound comprising a thiol group and an amino group. In certain embodiments, the cyclization moiety is an α,β-unsaturated carbonyl moiety. In some embodiments, the probe is capable of undergoing a condensation/cyclization reaction with Cys and/or Hcy. In certain embodiments, the α,β-unsaturated carbonyl moiety is capable of undergoing condensation/cyclization with both Cys and Hcy, but with measurably different reaction rates. In particular embodiments, the probe is capable of producing an emission spectrum maximum at a first wavelength after condensation with a thiol-containing compound, and the probe further is capable of producing an emission spectrum maximum at a second wavelength after condensation with a compound comprising a thiol group and an amino group and subsequent cyclization of the compound with cleavage and release of the fluorophore moiety, wherein the first and second wavelengths are not the same. In general, fluorophores that form O-acyl or N-acyl groups when conjugated to the α,β-unsaturated carbonyl moiety may be suitable fluorophore moieties.

One suitable fluorophore is 2-(2'-hydroxyphenyl)benzothiazole (HBT) (FIG. 1). As shown in FIG. 1, HBT can undergo an excited-state intramolecular photon transfer (ESIPT) process upon photo excitation whereby rapid photoinduced proton transfer results in tautomerization between its enol and keto forms. The enol form produces fluorescent emission at a short wavelength, and the keto form produces fluorescent emission at a long wavelength. Accordingly, HBT exhibits dual emission bands, which originate from its enol and keto tautomeric forms (Lochbrunner et al., *J. Chem. Phys.* 2000, 112, 10699-10702). Modifying the hydroxyl group of HBT blocks ESIPT, resulting exclusively in enol-like emission. If the free hydroxyl group is regenerated, tautomerization resumes and dual emission bands reappear.

The inventors hypothesized that masking the hydroxyl group of HBT with an α,β-unsaturated carbonyl moiety capable of undergoing a condensation/cyclization reaction with Cys and/or Hcy might generate a probe capable of distinguishing between Cys and Hcy, wherein the probe would be capable of dual fluorescence emission (upon excitation with a light source) after the α,β-unsaturated carbonyl moiety was removed by the condensation/cyclization reaction.

The probe would emit little or no fluorescence prior to condensation with the thiol group. After condensation, the probe would emit fluorescence at the wavelength corresponding to the enol form, and the fluorescence from the keto form would increase over time as the reaction progressed with cyclization of Cys and/or Hcy and concomitant release of the fluorophore moiety. The fluorescence from the keto form would be expected to increase more slowly in the presence of Hcy than in the presence of Cys due to the difference in reaction rates. Although the probe may be capable of condensation with non-amino-containing thiols and/or thiols with a secondary or tertiary amino group e.g., glutathione, cyclization and release of the fluorophore is unlikely to occur.

In some embodiments, the probe comprises a fluorophore moiety derived from HBT or a derivative thereof wherein the fluorophore moiety has a chemical structure according to formula I

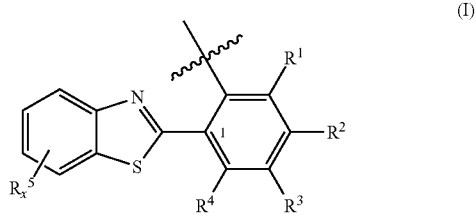

where $R^1$-$R^4$ independently are hydrogen, hydroxyl, halogen, thiol, thioether, lower aliphatic, or lower alkoxy, x is an integer from 0 to 4, and each $R^5$ independently is halogen, hydroxyl, thiol, thioether, lower aliphatic, or lower alkoxy. In some embodiments, upon cleavage of the cyclization moiety from the fluorophore moiety, a fluorophore comprising an electron donating group (e.g., hydroxyl, thiol, thioether, lower alkoxy) in a position ortho or meta to $C^1$ in general formula I is released. In certain embodiments, $R^1$ is methoxy. In particular embodiments, $R^1$ is methoxy, $R^2$-$R^4$ are hydrogen, and x is 0.

Suitable HBT derivatives include substituted hydroxyphenylbenzothiazoles. In certain embodiments, the fluorophore moiety is derived from 2-(2'-hydroxy-3'-methoxyphenyl)-benzothiazole (HMBT). HMBT has fluorescence emission bands at 377 nm (enol form) and 487 nm (keto form). In at least some embodiments, the presence of a 3' methoxy group (i.e., $R^1$=methoxy) provided stronger fluorescence at 377 nm than a corresponding probe where $R^1$ and $R^2$ were hydrogen.

The probe further comprises a cyclization moiety attached where indicated in general formula I. In some embodiments, the cyclization moiety is an α,β-unsaturated carbonyl moiety. In certain embodiments, the α,β-unsaturated carbonyl moiety is a substituted or unsubstituted acrylate ester moiety capable of reacting with a thiol group, e.g., a thiol group on Cys or Hcy. Suitable substituents may include halogen, hydroxyl, lower alkoxy, lower aliphatic, or aryl groups. In one embodiment, an acrylate ester substituted with a benzene ring on the α carbon (structure A) reacted poorly with thiol-containing compounds and demonstrated almost no response, perhaps due to steric hindrance from the benzene ring.

(A)

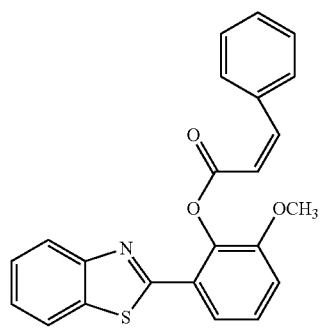

Thus, in certain embodiments, the acrylate ester is unsubstituted or includes substituents unlikely to produce steric hindrance, e.g., halogen, hydroxyl, lower alkoxy (such as methoxy, ethoxy) or lower aliphatic (such as methyl, ethyl, propyl) groups. In particular embodiments, the acrylate ester is unsubstituted and has the formula $H_2C=CHC(O)O-$.

In some embodiments, the probe has a structure according to general formula II (II)

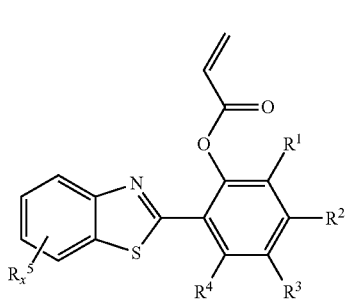

where $R^1$-$R^4$ independently are hydrogen, hydroxyl, halogen, thiol, thioether, lower aliphatic, or lower alkoxy, x is an integer from 0 to 4, and each $R^5$ independently is halogen, hydroxyl, thiol, thioether, lower aliphatic, or lower alkoxy. In certain embodiments, $R^1$ is methoxy. In one embodiment, $R^1$ is methoxy, $R^2$-$R^4$ are hydrogen, and x is zero (i.e., probe 4).

Probe 4

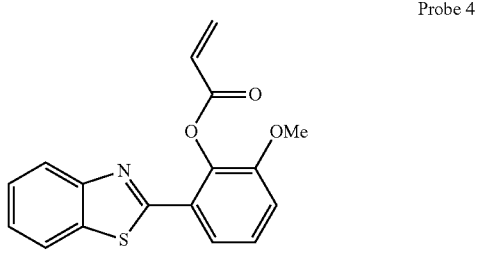 [SMILES: C=CC(=O)Oc1c(OC)cccc1-c1nc2ccccc2s1]

V. PROBE SYNTHESIS

In some embodiments, a probe is synthesized using HBT or HMBT as the fluorophore moiety. HMBT can be synthesized by reacting 2-aminothiophenol with o-vanillin in ethanol. An α,β-unsaturated carbonyl moiety is added by acylating the free hydroxyl group on the fluorophore with an acrylic acid derivative, e.g., acryloyl chloride. The synthesized probes typically are only weakly fluorescent due to quenching of the fluorophore by the carbon-carbon double bond via a photo-induced electron transfer (PET) process.

VI. CYSTEINE AND HOMOCYSTEINE DETECTION AND DIFFERENTIATION

Embodiments of the disclosed probes are capable of undergoing condensation and cyclization with at least some compounds that include a thiol group and an amino group. In some embodiments, the probes are capable of undergoing condensation/cyclization with compounds that include a terminal thiol group and a primary amino group, e.g., cysteine and/or homocysteine. Some embodiments of the disclosed probes may be capable of undergoing a condensation reaction without subsequent cyclization with other thiol-containing compounds, such as thiol compounds that include no amino group and/or thiol compounds that include a secondary or tertiary amino group.

Probe 4 reacts with Cys (n=1) and Hcy (n=2) as shown in Scheme 2.

Scheme 2

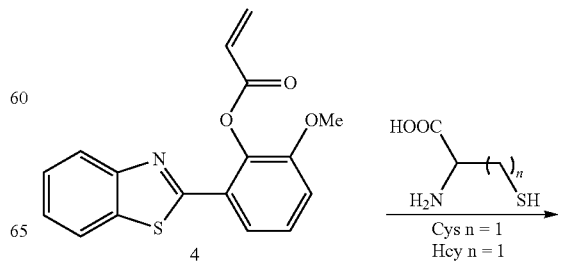

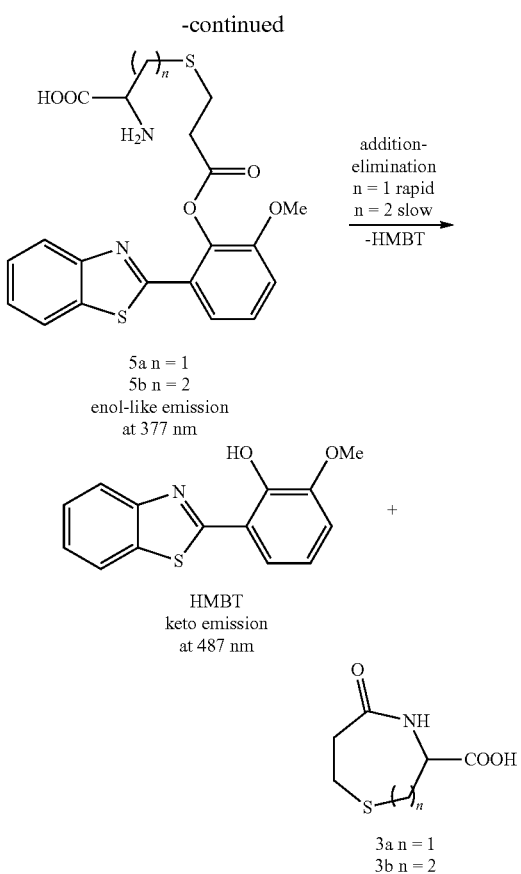

As shown in Scheme 2, the acrylate ester moiety of probe 4 combines with the thiol group in cysteine and homocysteine to form compounds 5a and 5b, respectively. Subsequent cyclization of Cys and Hcy with the acrylate ester moiety and concomitant elimination of HMBT produces cyclic compounds 3a and 3b, respectively.

In some embodiments, a probe according to general formula II is combined in solution with a sample potentially including at least one compound having a thiol group and an amino group. A reaction between the compound and the probe is allowed to proceed for an effective period of time. In some embodiments, the reaction is performed at a temperature ranging from 0° C. to 95° C., such as 10° C. to 60° C., 15° C. to 50° C., or 20° C. to 30° C. In certain embodiments, the reaction is performed at ambient temperature. An effective period of time is an amount of time sufficient to allow condensation and/or cyclization to occur. The effective period of time may depend, at least in part, on the reaction temperature. In some embodiments, an effective period of time is at least 5 minutes at least 7 minutes, at least 9 minutes, or at least 10 minutes. In certain embodiments, effective periods of time range from 5 minutes to 20 hours, such as 5 minutes to 15 hours, 5 minutes to 5 hours, 5 minutes to 2 hours, 5-75 minutes, 5-60 minutes, 5-40 minutes, or 9-60 minutes. In some embodiments, the reaction is performed at physiologic pH, e.g., a pH of 7-8, such as a pH of 7.3-7.5. In certain embodiments, the reaction is performed at pH 7.4.

After the effective period of time, the at least one compound can be detected by fluorescence. In some embodiments, a fluorescence spectrum over a range of wavelengths, e.g., 200-600 nm is obtained after the effective period of time. In certain embodiments, a plurality of fluorescence spectra are obtained over a period of time ranging from zero minutes to a time greater than or equal to the effective period of time. For example, a plurality of spectra may be obtained over a time period ranging from zero minutes to 20 hours, 0 minutes to 15 hours, 0 minutes to 2 hours, 0-75 minutes, 0-60 minutes, 0-40 minutes, 5-75 minutes, 5-60 minutes, 5-40 minutes, or 5-30 minutes.

In some embodiments, fluorescence is measured or monitored at one or more wavelengths corresponding to expected emission spectrum maxima of the probe. For example, when the probe is probe 4, fluorescence may be measured or monitored at 377 nm (corresponding to the enol form of probe 4) and/or 487 nm (corresponding to the keto form of probe 4). If fluorescence at 377 nm is detected after the effective period of time, it indicates that the solution includes at least one compound capable of undergoing condensation with probe 4. If fluorescence at 487 nm is detected after the effective period of time, it indicates that the solution includes at least one compound capable of undergoing condensation with probe 4 and subsequent cyclization with release of the fluorophore moiety.

Figure 2:
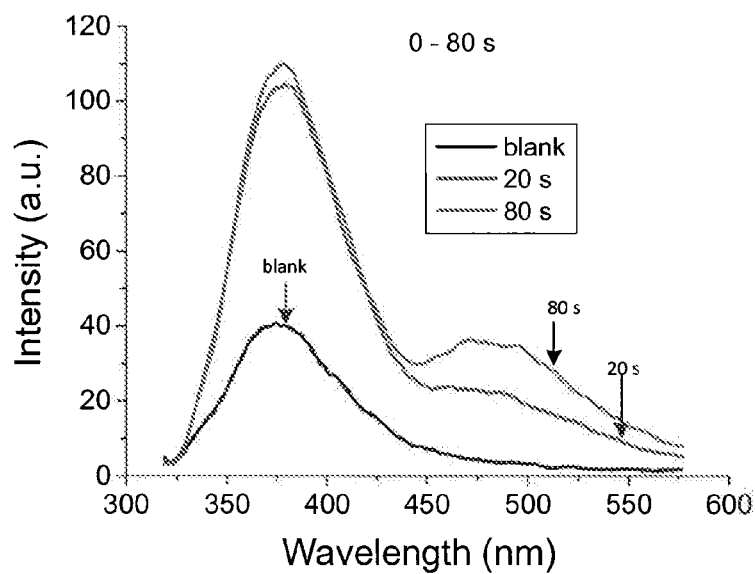
FIG. 2 is a graph of absorbance intensity versus wavelength for the reaction of probe 4 with cysteine over a time period of 0-80 seconds. $\lambda_{ex}$=304 nm.
Figures 3A, 3B:
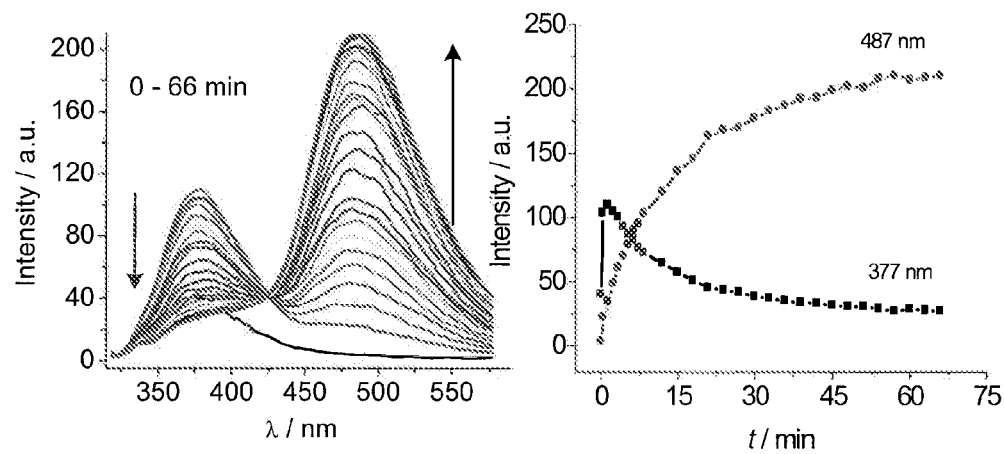
FIG. 3A is a graph of absorbance intensity versus wavelength for the reaction of probe 4 with cysteine over a time period of 0-66 minutes. $\lambda_{ex}$=304 nm.
FIG. 3B is a graph of absorbance intensities at 377 nm and 487 nm versus time for the reaction of probe 4 with cysteine over a time period of 0-66 minutes. $\lambda_{ex}$=304 nm.
Figure 4:
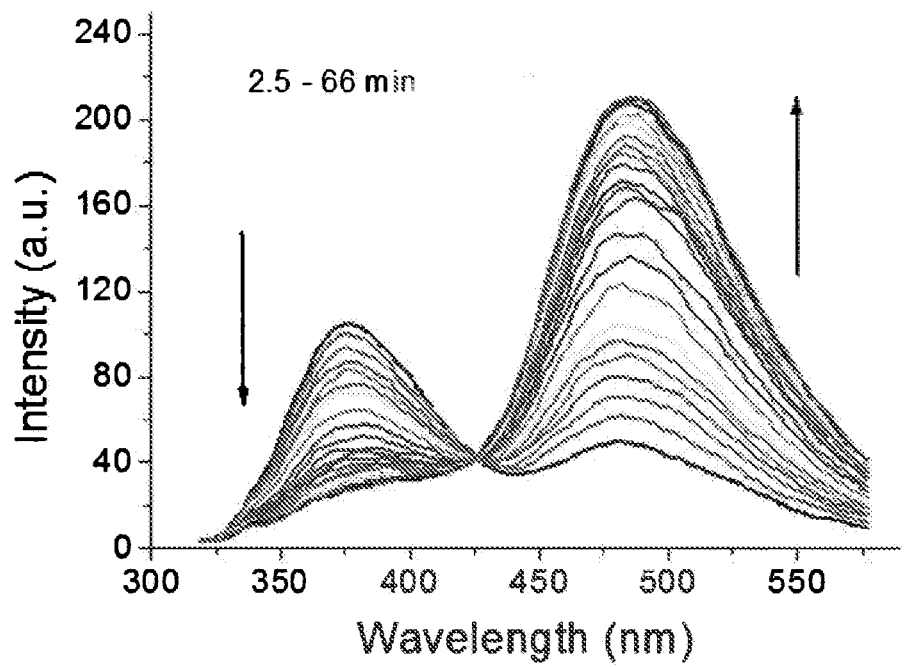
FIG. 4 is a graph of absorbance intensity versus wavelength for the reaction of probe 4 with cysteine over a time period of 2.5-66 minutes, illustrating an isoemissive point at 427 nm. $\lambda_{ex}$=304 nm.

In a working embodiment, fluorescence evaluation of the reaction between probe 4 and Cys demonstrated that emission at 377 nm increases initially due to conjugate addition which removes the alkene-induced PET quenching (FIG. 2). Upon further reaction, the emission band at 377 nm successively decreases with concomitant growth of the keto band at 487 nm (FIGS. 3A-B). A well-defined isoemissive point appears at 427 nm (FIG. 4). The latter spectral change is due to lactam formation which results in the formation of HMBT exhibiting ESIPT.

Figure 5:
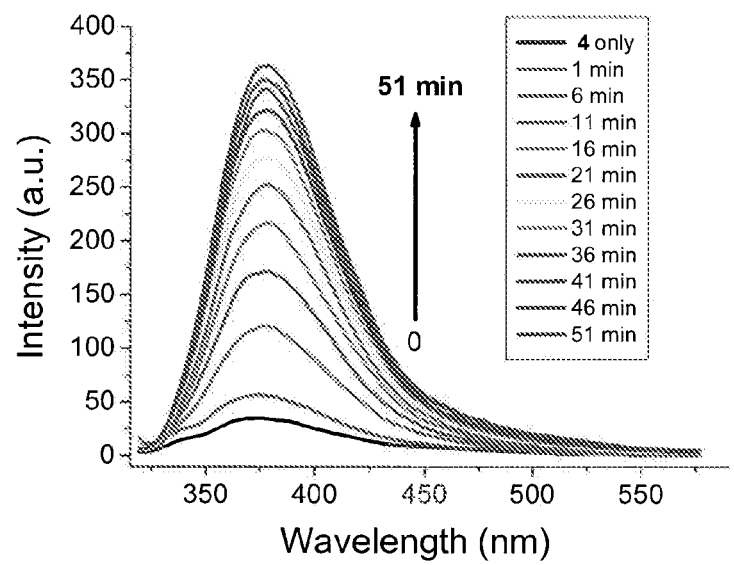
FIG. 5 is a graph of absorbance intensity versus wavelength illustrating the time-dependent fluorescence spectral changes of 4 (20 µM) with Hcy (1 equiv) in EtOH:phosphate buffer (20 mM, pH 7.4, 2:8 v/v) over a time period of 0-51 minutes. $\lambda_{ex}$=304 nm.
Figure 6:
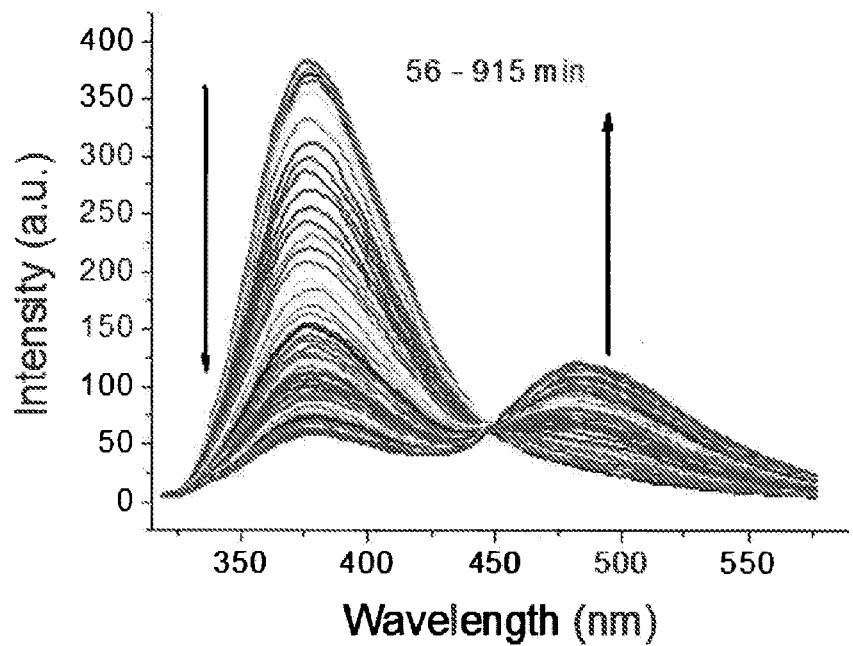
FIG. 6 is a graph of absorbance intensity versus wavelength illustrating the time-dependent fluorescence spectral changes of 4 (20 µM) with Hcy (1 equiv) in EtOH:phosphate buffer (20 mM, pH 7.4, 2:8 v/v) over a time period of 56-915 minutes. $\lambda_{ex}$=304 nm.
Figures 7A, 7B:
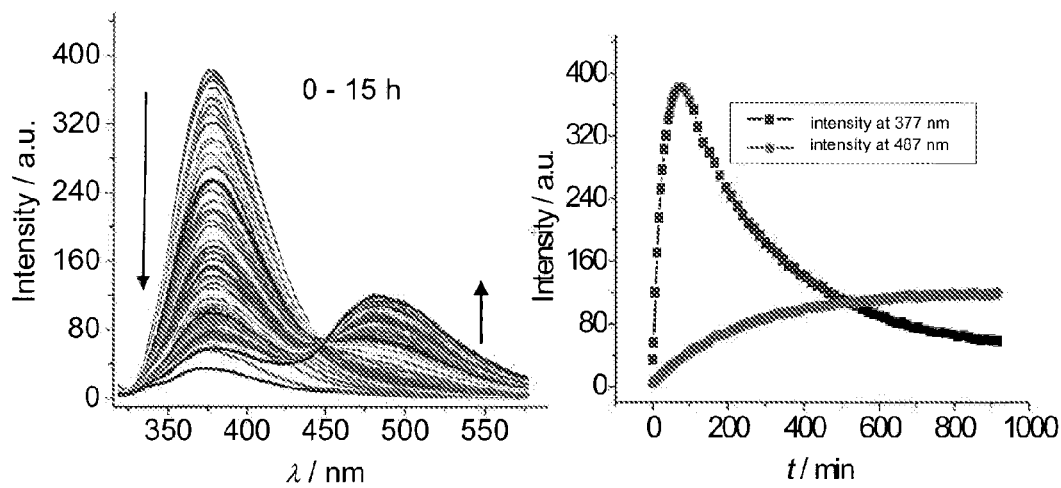
FIG. 7A is a graph of absorbance intensity versus wavelength for the reaction of probe 4 with homocysteine over a time period of 0-15 hours. $\lambda_{ex}$=304 nm.
FIG. 7B is a graph of absorbance intensities at 377 nm and 487 nm versus time for the reaction of probe 4 with cysteine over a time period of 0-1000 minutes. $\lambda_{ex}$=304 nm.

In the case of Hcy, the conjugate addition reaction leads to thioether 3b. However, the rate for subsequent eight-membered ring lactam formation 3b is relatively slow compared to the formation of 3a. In a working embodiment, emission at 377 nm steadily increased over time for 55 minutes (FIG. 5), followed by a decrease in emission at 377 nm after 55 minutes accompanied by an increase of the emission at 487 nm (FIG. 6, FIGS. 7A-B).

Figure 9:
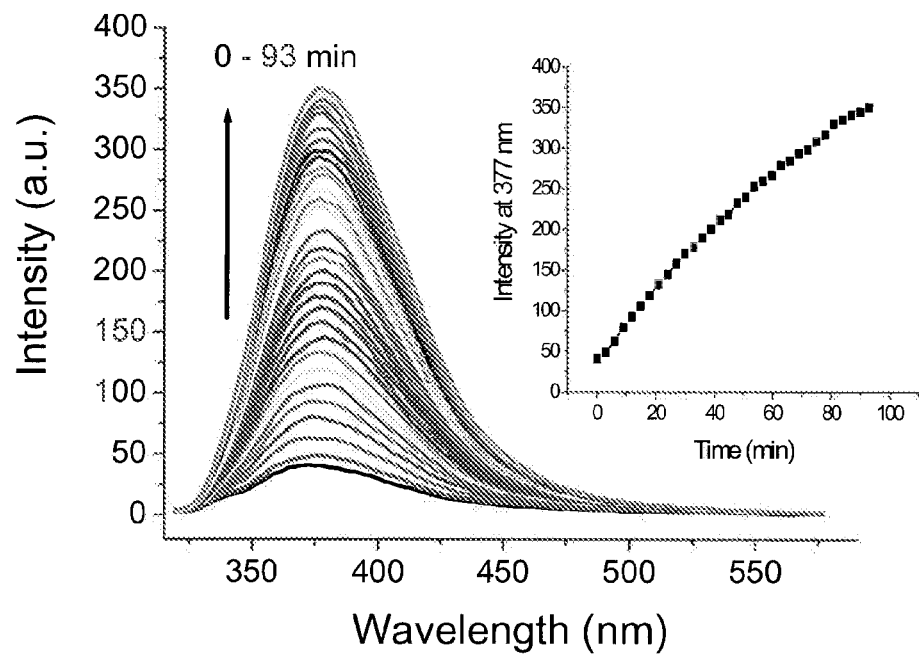
FIG. 9 is a graph of absorbance intensity versus wavelength illustrating the time-dependent fluorescence spectral changes of probe 4 (20 μM) with 3-mercaptopropanoic acid (91.2 μM) in EtOH:phosphate buffer (20 mM, pH 7.4, 2:8 v/v). $\lambda_{ex}$=304 nm. Inset: Time-dependent fluorescence intensity changes at 377 nm.
Figure 10:
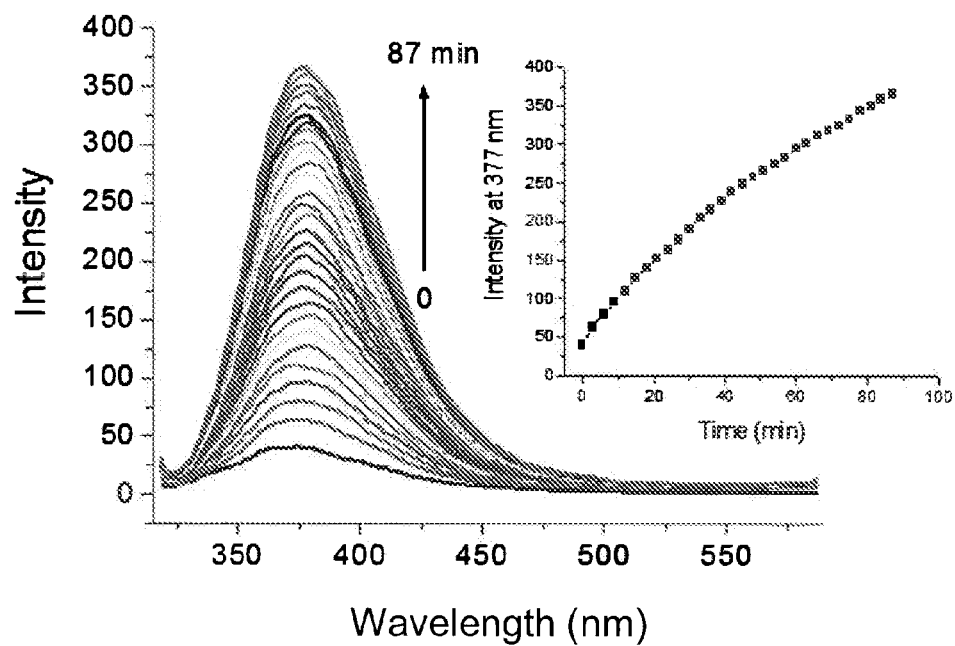
FIG. 10 is a graph of absorbance intensity versus wavelength illustrating the time-dependent fluorescence spectral changes of probe 4 (20 μM) with N-acetyl-L-cysteine (20 μM) in EtOH:phosphate buffer (20 mM, pH 7.4, 2:8 v/v). $\lambda_{ex}$=304 nm. Inset: Time-dependent fluorescence intensity changes at 377 nm.

Control experiments demonstrate that the amino group of Cys is needed for the selective cyclization reaction. When cysteamine was reacted with probe 4, similar fluorescence changes are observed as for Cys under analogous reaction conditions (FIGS. 8A-D). However, 3-mercaptopropanoic acid (MPA) exhibits fluorescence emission centered at 377 nm due to the formation of the conjugate addition product only (FIG. 9). N-acetyl-L-cysteine (NAC) produces a similar result to that of MPA, formation of the conjugate addition adduct (FIG. 10). Thus, the amino group is involved in the intramolecular cyclization reaction, and the reaction does not occur in the absence of the amino group.

Figure 11:
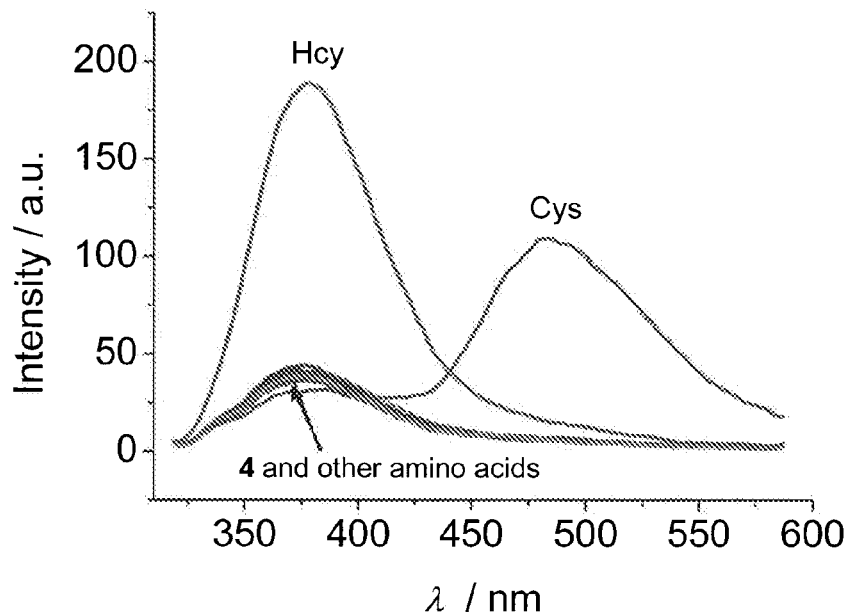
FIG. 11 is a series of fluorescence spectra of probe 4 with various amino acids (Cys, Hcy, leucine, proline, arginine, histidine, valine, methionine, threonine, glutamine, alanine, aspartic acid, norleucine, isoleucine, lysine, cystine and homocystine) after 40 min. $\lambda_{ex}$=304 nm.

Probe selectivity for Cys and Hcy was demonstrated by evaluating changes in fluorescence intensity of 4 caused by other analytes, such as leucine, proline, arginine, histidine, valine, methionine, threonine, glutamine, alanine, aspartic acid, norleucine, isoleucine, lysine, cystine and homocystine. As shown in FIG. 11, only Cys and Hcy exhibited significant fluorescence intensity changes at 487 and 377 nm, respectively, after 40 minutes while other amino acids caused no fluorescence intensity changes under the same conditions.

Figure 15:
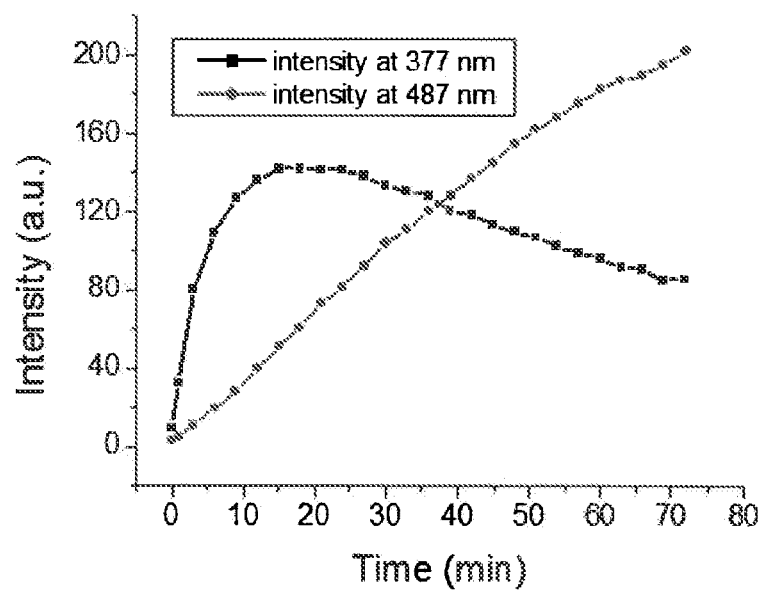
FIG. 15 is a graph of absorbance intensity versus time at 377 nm and 487 nm illustrating the time-dependent fluorescence spectral changes of probe 4 (10 μM) with Hcy (2 equiv) in CTAB media (1.0 mM) buffered at 7.4 (phosphate buffer, 20 mM). $\lambda_{ex}$=304 nm.
Figure 16:
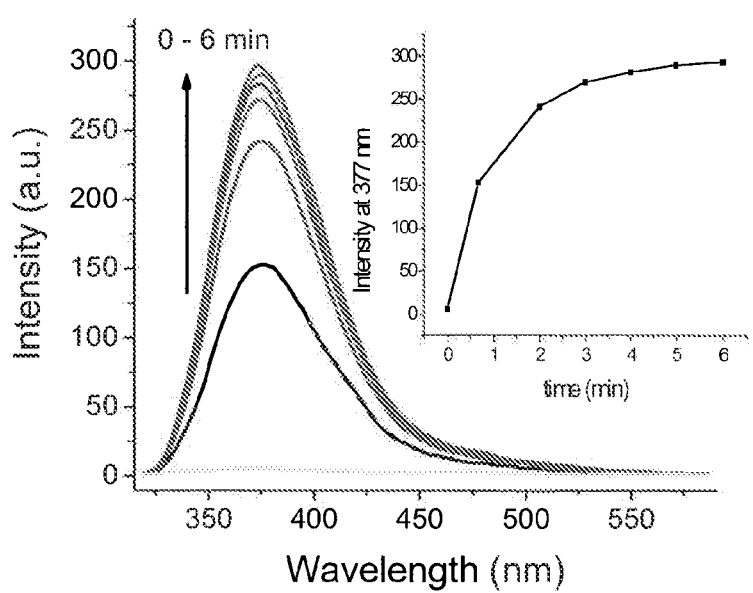
FIG. 16 is a graph of absorbance intensity versus wavelength illustrating the time-dependent fluorescence spectral changes of probe 4 (10 μM) with GSH (2 equiv) in CTAB media (1.0 mM) buffered at 7.4 (phosphate buffer, 20 mM). $\lambda_{ex}$=304 nm. Inset: time-dependent fluorescence intensity changes at 377 nm.
Figure 17:
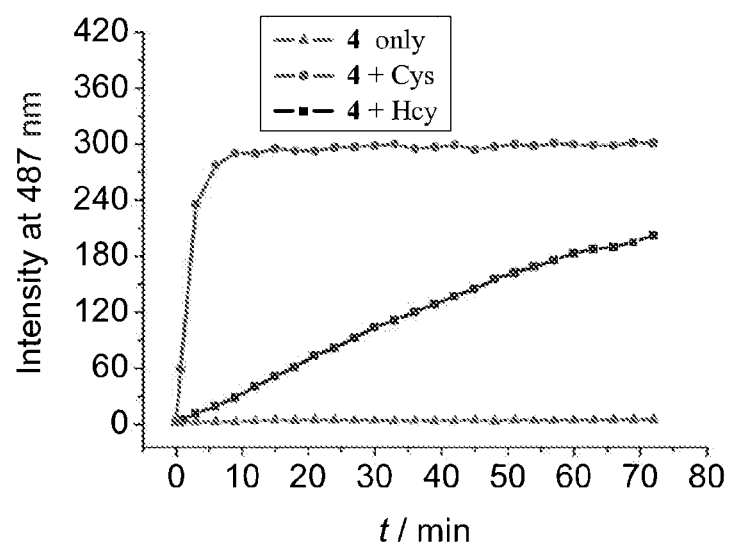
FIG. 17 is a graph of absorbance intensity versus time at 487 nm illustrating the time-dependent fluorescence intensity changes of probe 4 (10 μM) at 487 nm upon adding Cys or Hcy (both 20 μM) in CTAB media (1.0 mM) buffered at 7.4 (phosphate buffer, 20 mM). $\lambda_{ex}$=304 nm.

GSH can also react with embodiments of the disclosed probes to produce enol-like emission due to the conjugate addition reaction (see, e.g., FIG. 12), potentially interfering with Cys and/or Hcy detection. However, GSH and other sulfhydryls are not capable of cyclizing and releasing the fluorophore; thus, GSH and other sulfhydryls do not produce fluorescence emission at 487 nm when reacted with probe 4, but may produce fluorescence emission at 377 nm. Interference from GSH and other sulfhydryls can be overcome by addition of a surfactant that increases the cyclization and release rates of Cys and Hcy. In some embodiments, the surfactant is a cationic surfactant, such as a quaternary ammonium surfactant. In one embodiment, the surfactant was cetyltrimethylammonium bromide (CTAB). Surfactants such as CTAB increase the reaction rate of Cys and Hcy with probe 4, resulting in a more rapid increase in fluorescence emission at 487 nm (FIGS. 13-16). As shown in FIG. 17, the formation of HMBT from probe 4 and Cys is complete within 9 minutes. In the case of Hcy, almost no free HMBT emission can be observed in 9 minutes (FIG. 17); however, HMBT emission at 487 nm increases over time, allowing Hcy to be distinguished from GSH and other sulfhydryls that are incapable of cyclization with release of the fluorophore.

The detection limits of Cys and Hcy are 0.11 μM and 0.18 μM, respectively, which is below the requisite detection limits for Cys and Hcy in human plasma. The assay can distinguish concentration changes on the order of 2-3 μM. Such sensitivity enables sensitivity distinguish, for instance, normal (5-12 μM) Hcy levels, hyperhomocysteinemia (16-100 μM, indicating cardiovascular risk) and homocysteinuria (>100 μM, a severe inherited metabolic disorder associated with mental retardation, a multisystemic disorder of the connective tissues, muscles, central nervous system, and cardiovascular system).

Thus, in some embodiments of the disclosed method, a solution comprising a probe according to general formula II and a surfactant is combined with a sample potentially including at least one compound having a thiol group and an amino group. The reaction is allowed to progress for an effective period of time, and the at least one compound is detected by detecting fluorescence of the solution. In certain embodiments, the surfactant is cetyltrimethylammonium bromide. In particular embodiments, R is methoxy. When R is methoxy, fluorescence can be monitored at 377 nm and/or 487 nm to detect the at least one compound. If the at least one compound is cysteine, fluorescence can be detected at 487 nm after the effective period of time. In some embodiments, when the at least one compound is homocysteine, fluorescence can be detected at 377 nm substantially immediately after the effective period of time, e.g., at 8-10 minutes after combining the sample and the probe solution. In certain embodiments when the at least one compound is homocysteine, fluorescence of the solution is measured at 377 nm and 487 nm substantially immediately after the effective period of time and again at a second, later time. The difference in the fluorescence measurements at the first and second times at each wavelength is determined. If homocysteine is present, a decrease in fluorescence at 377 nm and a proportional increase in fluorescence at 487 nm will be observed.

In some embodiments, the sample may further include glutathione and/or non-amino thiols. Glutathione and other non-amino thiols may undergo condensation with the probe, but are unable to subsequently cyclize and release the fluorophore. Thus, in such embodiments, Cys can be measured via a stable signal (i.e., stable fluorescence intensity) appearing at 487 nm substantially immediately after the effective period of time, e.g., after 8-10 minutes after (indicating rapid condensation and cyclization). As used herein with respect to fluorescence intensity, the term "stable" means that the fluorescence intensity changes by less than 20%, such as less than 15%, less than 10%, less than 5% or less than 2% over a subsequent period of time. In some embodiments, the fluorescence intensity remains stable for a subsequent period of time of at least 5 additional minutes, at least 10 additional minutes, at least 15 additional minutes, at least 30 additional minutes, or at least 45 additional minutes, such as 5-60 additional minutes, 5-55 additional minutes, 10-50 additional minutes, or 15-45 additional minutes following the effective period of time. GSH and non-amino thiols can be measured via a stable signal at 377 nm after the effective period of time (indicating condensation but no cyclization). Hcy is the only analyte that causes a proportional change of the signals at 377 nm and 487 nm after the effective period of time as it slowly cyclizes with release of the fluorophore. Accordingly, Hcy can be detected by monitoring fluorescence over time because the respective signals due to Cys (487 nm) and other sulfhydryls (377 nm) stabilize after 9 minutes.

VII. KITS

Kits are also a feature of this disclosure. Embodiments of the kits include at least one probe according to general formula II, wherein the probe is suitable for selectively detecting one or more thiol-containing compounds, particularly one of more compounds including a thiol group and an amino group (e.g., cysteine, homocysteine). In certain embodiments, R in general formula II is methoxy. In some embodiments, the kit further includes a buffer solution at physiologic pH. In certain embodiments, the buffer is a phosphate buffer at pH 7-8, such as a 20 mM phosphate buffer at pH 7.4. The probe may be dissolved in the buffer, or the probe may be included in a dry form and the user can combine the probe and the buffer solution at or before the time of use. In some embodiments, the buffer solution further includes a surfactant, e.g., cetyltrimethylammonium bromide. The kits also may include one or more containers, such as a disposable test tube or cuvette, in which the detection can be performed. In some embodiments, an amount of the probe effective to undergo a detectable change in the fluorescence emission spectrum, or both when reacted with the at least one compound is premeasured into the disposable containers. The kits may further include instructions for performing the detection. In some embodiments, the kits include control samples of thiol-containing compounds, e.g., cysteine and/or homocysteine. Typically the control samples are provided in solid form.

VIII. EXAMPLES

Materials and Instruments

All chemicals were purchased from Sigma-Aldrich and Acros and used without further purification. $^1$H-NMR and $^{13}$C-NMR spectra were recorded on a Bruker AMX-400 NMR spectrometer, using TMS as an internal standard. ESI-HRMS (high resolution mass spectrometry) spectra were obtained on a Thermo Electron LTQ Orbitrap hybrid mass spectrometer. UV-visible spectra were collected on a Cary 50 UV-Vis spectrophotometer. Fluorescence spectra were collected on a Cary Eclipse (Varian, Inc.) fluorescence spectrophotometer with slit widths set at 5 and 10 nm for excitation and emission, respectively. The pH measurements were carried out with an Orion 410A pH meter. In all experiments enantiomerically pure natural amino acids were used except for homocysteine, which was used as the racemate.

Example 1

Synthesis of Probe 4

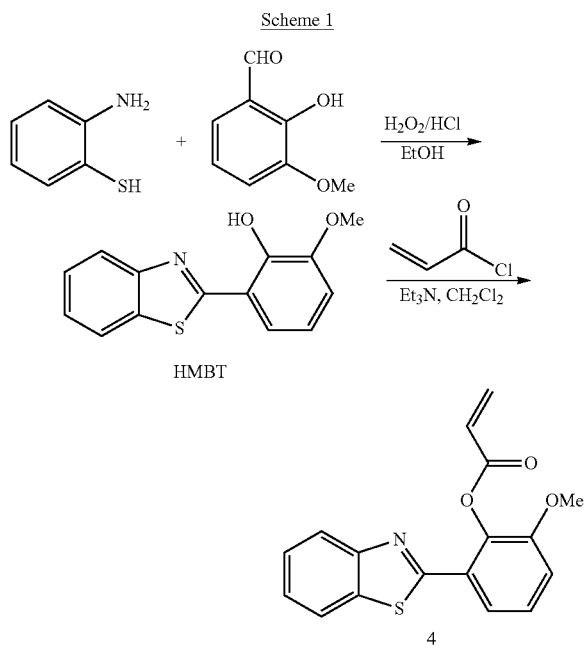

2-(2'-hydroxy-3'-methoxyphenyl)benzothiazole
(HMBT)

HMBT was synthesized according to a previous reported method with minor modifications (Guo et al., *Chin. Chem. Lett.* 2009, 20, 1408-1410. A solution of 2-aminothiophenol (0.3 mL, 4.2 mmol) and o-vanillin (0.48 g, 3.15 mmol) in EtOH (10 mL), aq $H_2O_2$ (30%, 18.9 mmol) and aq HCl (37%, 9.45 mmol) was stirred at room temperature for 90 min. The solution was quenched by 10 mL $H_2O$. The precipitate was filtered, dried under vacuum and recrystallized from EtOH to afford the desired product as a light yellow solid (0.64 g, 79% yield). $^1$H NMR (CDCl$_3$, 400 MHz), δ (ppm): 12.75 (s, 1H), 8.01 (d, 1H, J=7.6 Hz), 7.91 (d, 1H, J=7.2 Hz), 7.51 (t, 1H, J=6.8 Hz), 7.42 (t, 1H, J=7.2 Hz), 7.33 (dd, 1H, $J_1$=1.2 Hz, $J_2$=8.0 Hz), 6.99 (dd, 1H, $J_1$=1.2 Hz, $J_2$=8.0 Hz), 6.91 (t, 1H, J=8.0 Hz), 3.96 (s, 1H). $^{13}$C NMR (CDCl$_3$, 100 MHz), δ 169,74, 151.86, 149.13, 148.29, 136.47, 132.70, 126.80, 125.66, 122.36, 121.59, 120.11, 119.23, 116.86, 114.21, 56.36. ESI-FTMS m/z=258.0587 [M+H]$^+$, calc. 258.0589 for $C_{14}H_{12}NO_2S$.
Probe 4

Figure 18:
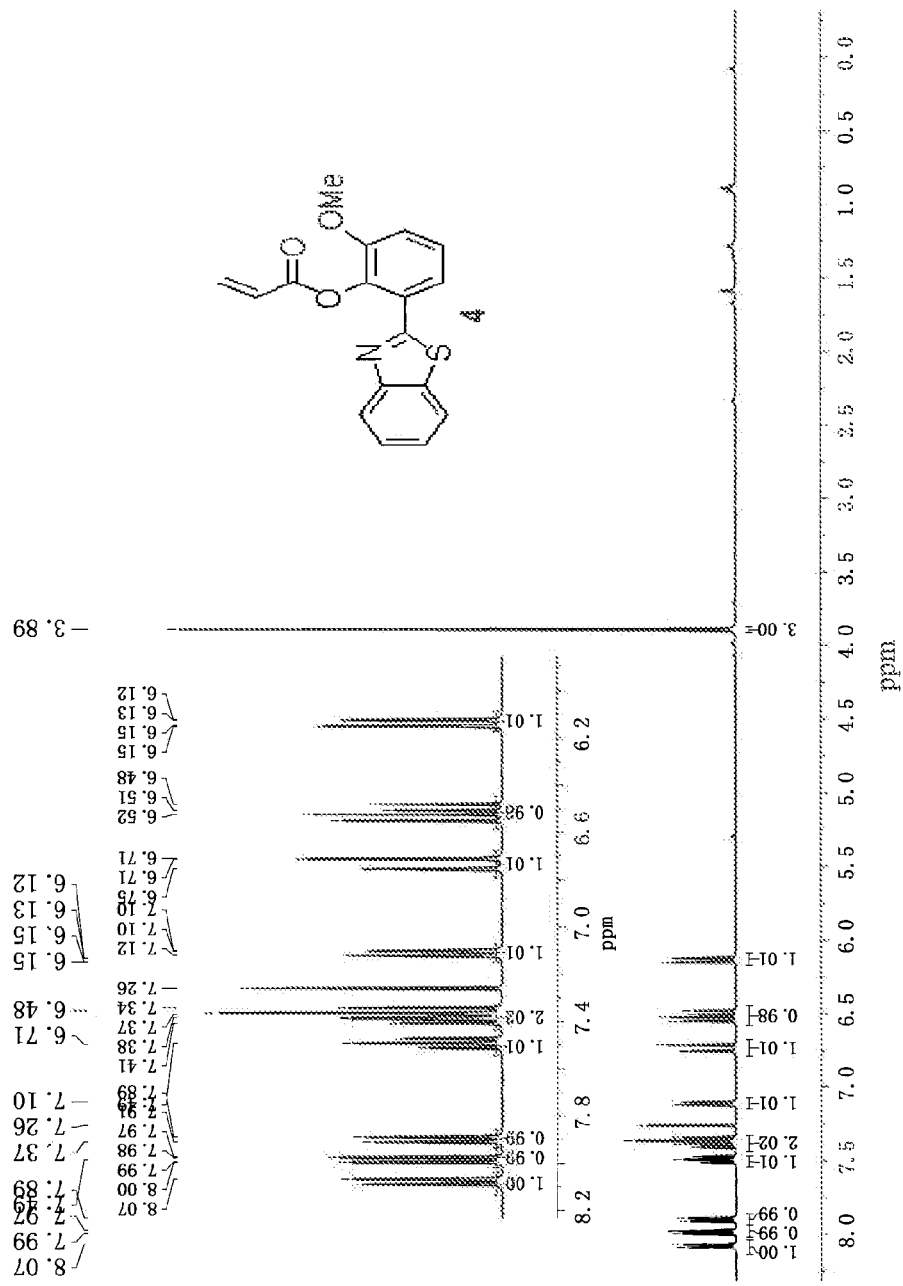
FIG. 18 is a $^1$H NMR (400 MHz) spectrum of probe 4 in CDCl$_3$.
Figure 19:
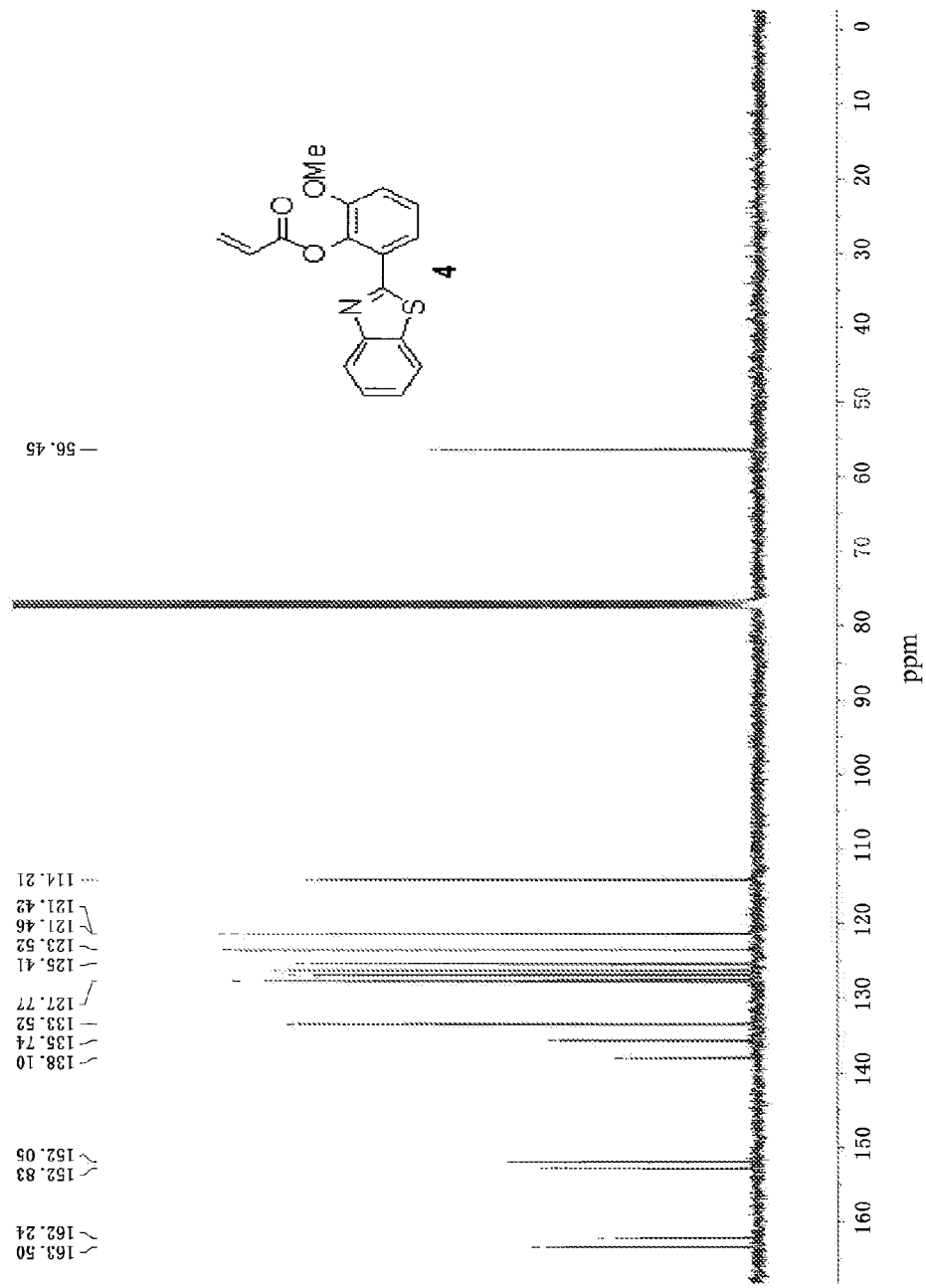
FIG. 19 is a $^{13}$C NMR (100 MHz) spectrum of probe 4 in CDCl$_3$.
Figure 20:
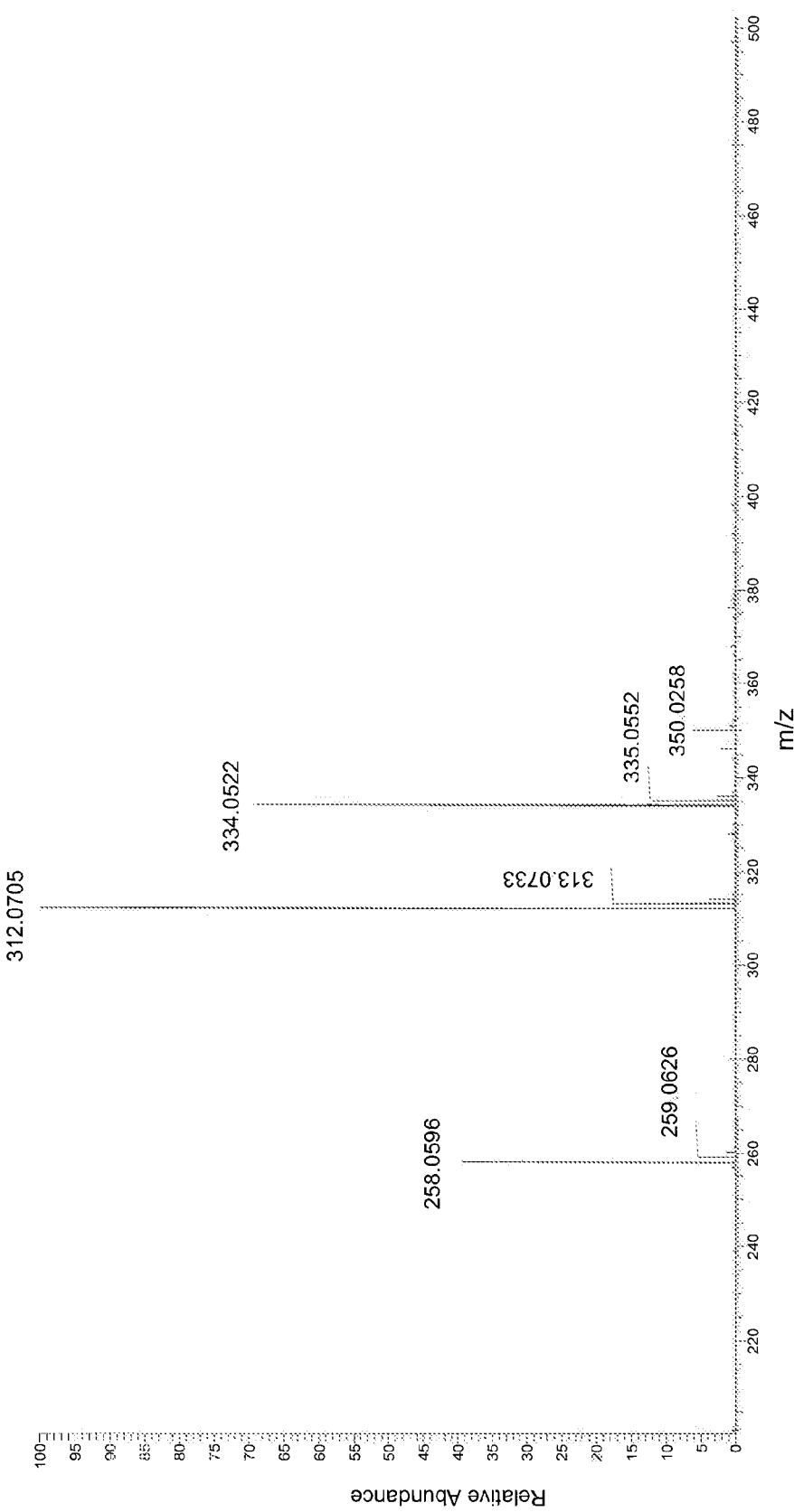
FIG. 20 is a high-resolution mass spectrum of probe 4 (a2-p 1104 19191754 #12-20; RT: 0.11-0.19; AV: 9; NL: 7.02E6; T: FTMS+p ESI Full ms [200.00-500.00]).

To a solution of HMBT (129 mg, 0.5 mmol) and Et$_3$N (2 eq) in 10 mL of anhydrous CH$_2$Cl$_2$, acryloyl chloride (1.25 eq, mixed with 4 mL of CH$_2$Cl$_2$) was added dropwise at 0° C. After stirring at this temperature 90 min, the mixture was warmed to room temperature and stirred overnight. The solution was diluted with CH$_2$Cl$_2$ (30 mL), washed with H$_2$O (15 mL×3) and dried over anhydrous Na$_2$SO$_4$. The solvent was removed in vacuo to furnish a crude mixture (dark brown oil) which afforded 4 upon crystallization from hexanes/CHCl$_3$ (20:1, v/v) as a light orange solid (110 mg, 71% yield). $^1$H NMR (CDCl$_3$, 400 MHz), δ (ppm) (FIG. 18): 8.08 (d, 1H, J=8.0 Hz), 7.99 (dd, 1H, $J_1$=1.6 Hz, $J_2$=8.0 Hz), 7.90 (d, 1H, J=8.0 Hz), 7.49 (t, 1H, J=7.2 Hz), 7.41-7.34 (m, 2H), 7.11 (dd, 1H, $J_1$=1.2 Hz, $J_2$=8.4 Hz), 6.74 (dd, 1H, $J_1$=1.2 Hz, $J_2$=17.6 Hz), 6.52 (m, 1H), 6.14 (d, 1H, $J_1$=1.2 Hz, $J_2$=10.4 Hz), 3.89 (s, 3H). $^{13}$C NMR (CDCl$_3$, 100 MHz) (FIG. 19), δ 163.50, 162.24, 152.83, 138.10, 135.74, 133.52, 127.77, 127.62, 126.91, 126.36, 125.82, 125.41, 123.52, 121.46, 121.42, 114.21, 56.45. ESI-FTMS (FIG. 20) m/z=312.0705 [M+H]$^+$, calc. 312.0694 for $C_{17}H_{14}NO_3S$.

Example 2

Condensation and Cyclization of Cysteine and Homocysteine with Probe 4

To a 100 mL flask, probe 4 (0.12 g, 3.85 mmol) and Cys (1.25 eq) were combined in 30 mL of MeOH:H$_2$O (90:10, v/v) solution, and the mixture stirred at room temperature for 1 hour. Triethylamine (Et$_3$N) (80 μL) was added, and the solution was stirred for about 40 minutes. The solvent was dried in vacuo, and the crude product was subjected to column chromatography (eluted with CH$_2$Cl$_2$:MeOH, 10:4, v/v) to afford 85 mg of HMBT and 49 mg of 3a as an off-white solid.

To a 100 mL flask, probe 4 (0.12 g, 3.85 mmol) and Hcy (1.25 eq) were combined in 30 mL of MeOH—H$_2$O (90:10, v/v) solution, and the mixture was stirred at room temperature for 4 hours. Et$_3$N (80 μL) was added and the solution stirred at room temperature overnight. The solvent was dried in vacuo and the crude product was subjected to column chromatography (eluted with CH$_2$Cl$_2$:MeOH, 10:6, v/v) to afford 78.2 mg of HMBT and 37.7 mg of 3b as an off-white solid.

Figure 21:
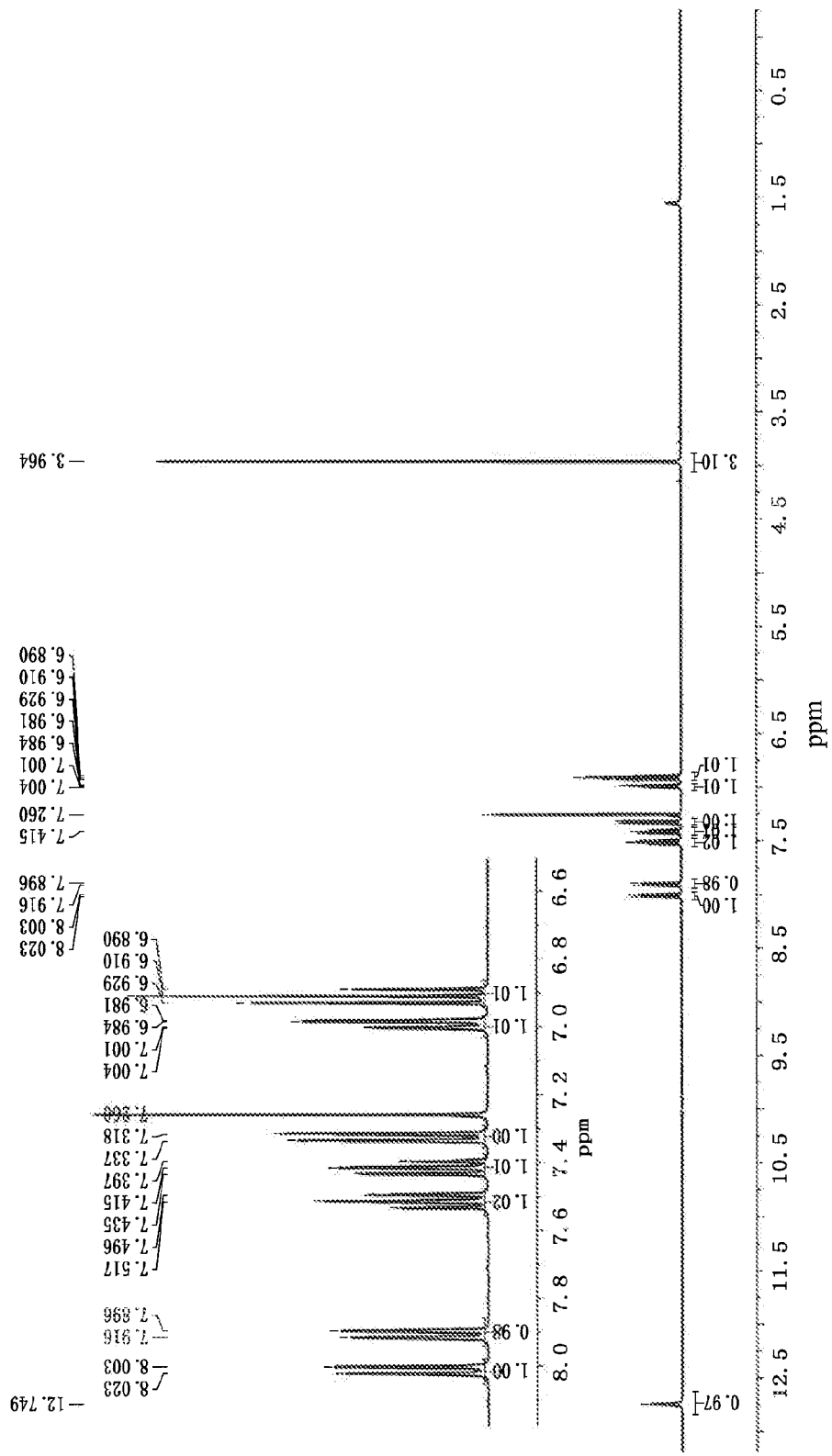
FIG. 21 is a $^1$H NMR (400 MHz) spectrum of HMBT in CDCl$_3$ obtained from the reaction of probe 4 with cysteine.
Figure 22:
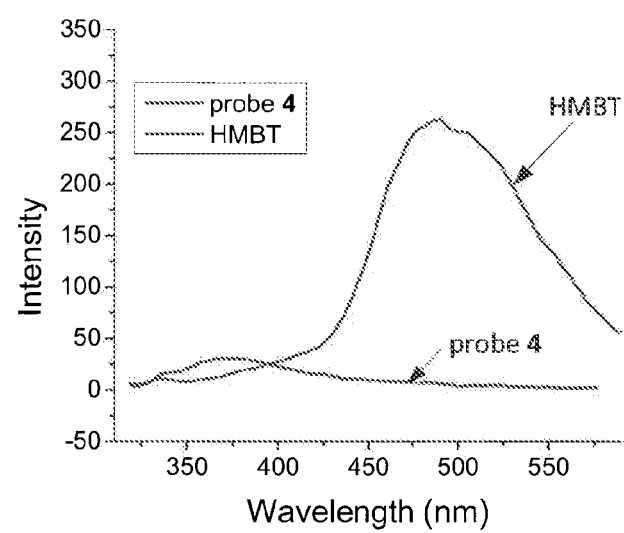
FIG. 22 is a graph of fluorescence intensity versus wavelength illustrating the fluorescence spectra ($\lambda_{ex}$=304 nm) of probe 4 and HMBT (both 10 μM) in EtOH:phosphate buffer (20 mM, pH 7.4, 2:8 v/v).
Figure 23:
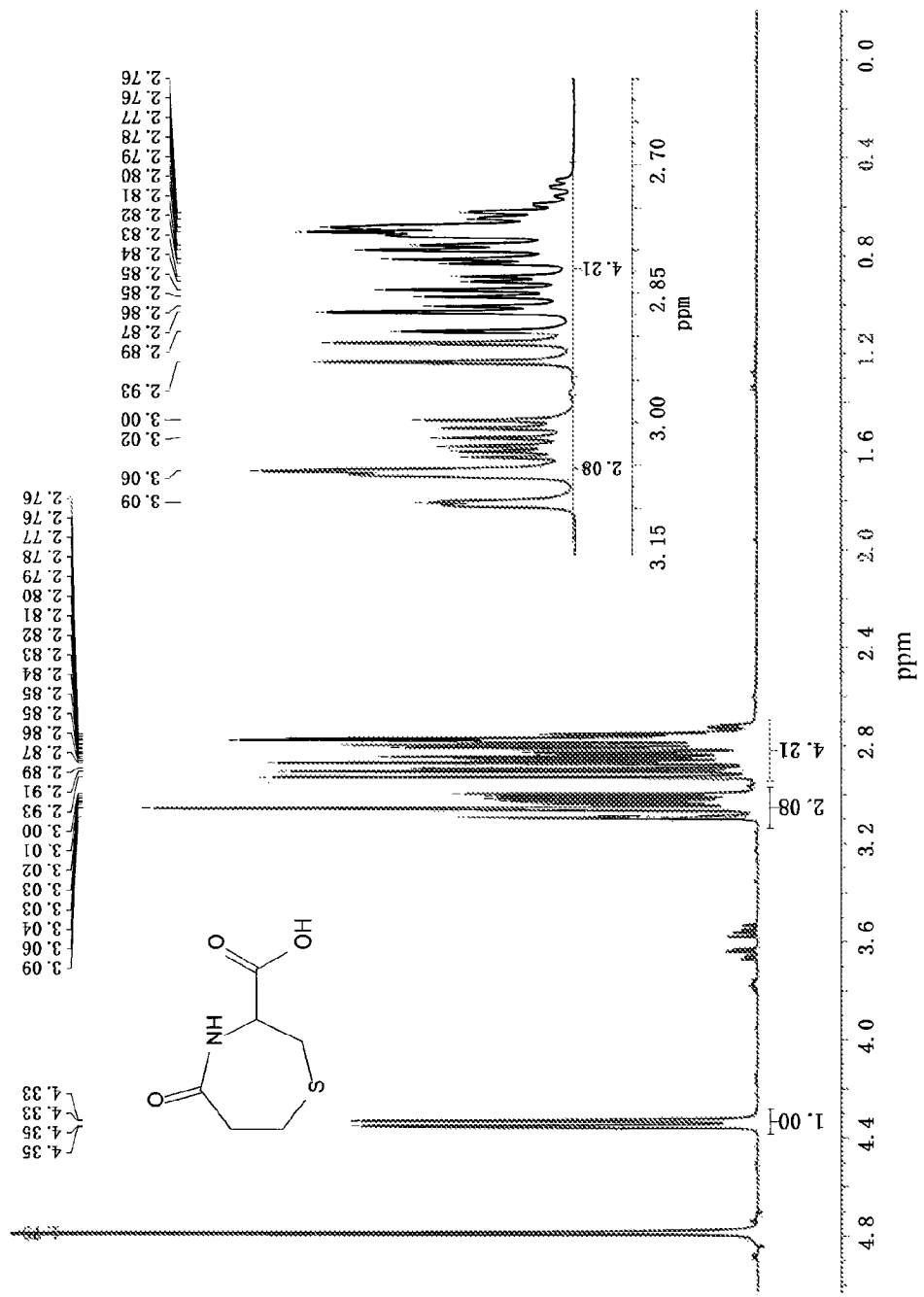
FIG. 23 is a $^1$H NMR (400 MHz) spectrum of compound 3a in D$_2$O.
Figure 24:
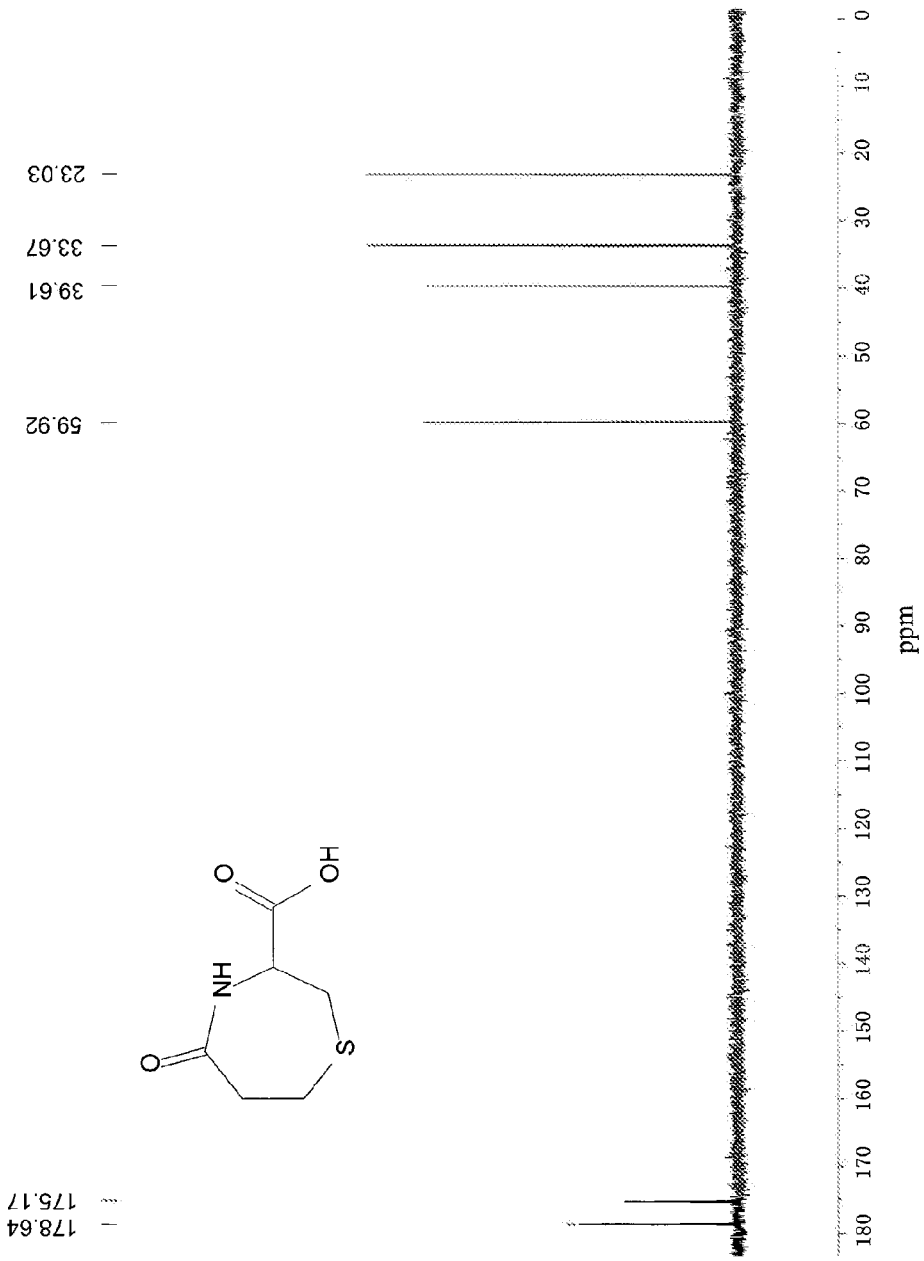
FIG. 24 is a $^{13}$C NMR (100 MHz) spectrum of compound 3a in D$_2$O.
Figure 25:
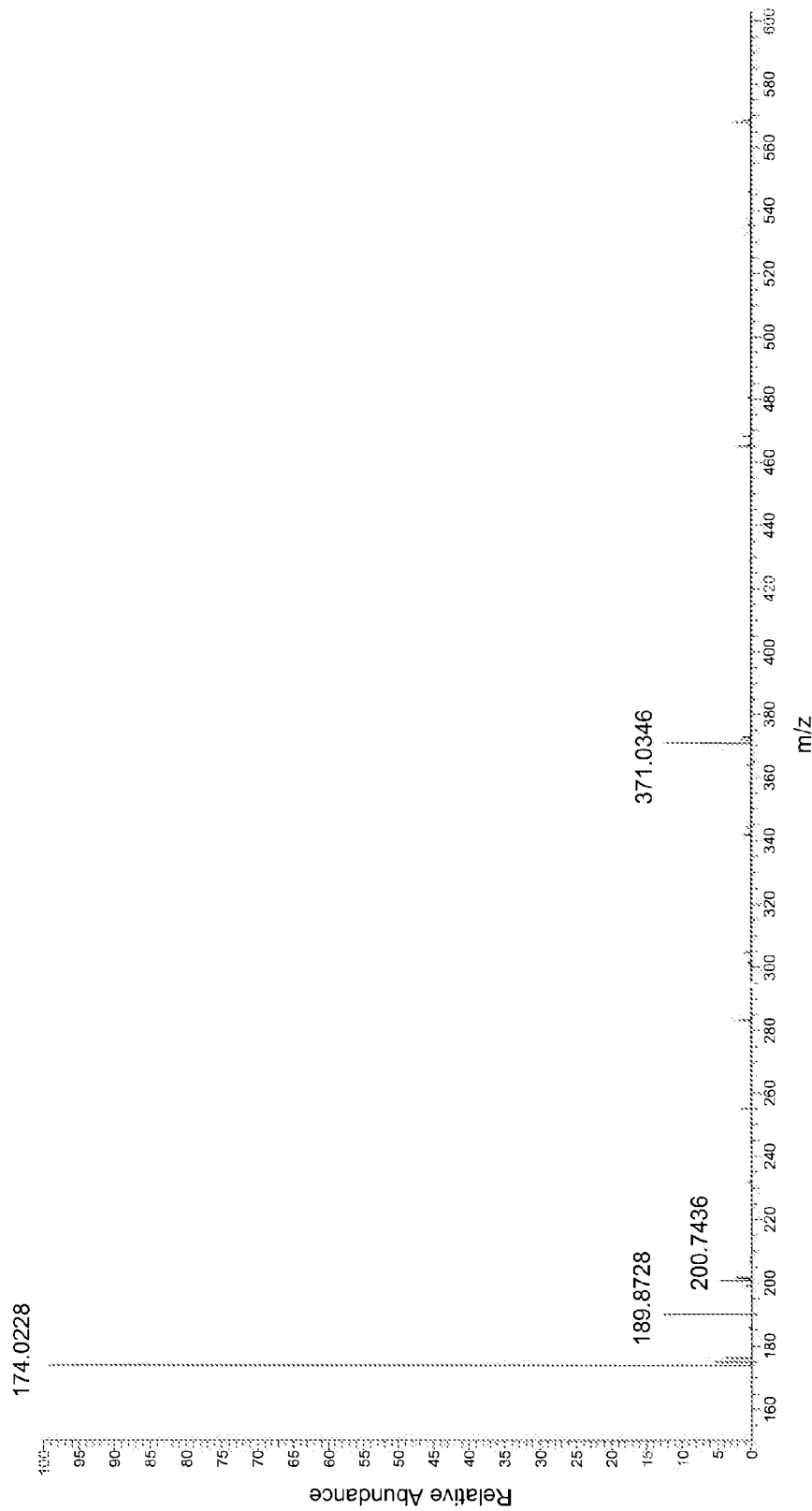
FIG. 25 is a high-resolution mass spectrum of compound 3a (5-n2 1104191745 #8-13; RT: 0.12-0.20; AV: 6; NL 1.30E5; T: FTMS−p ESI Full ms [150.00-600.00]).
Figure 26:
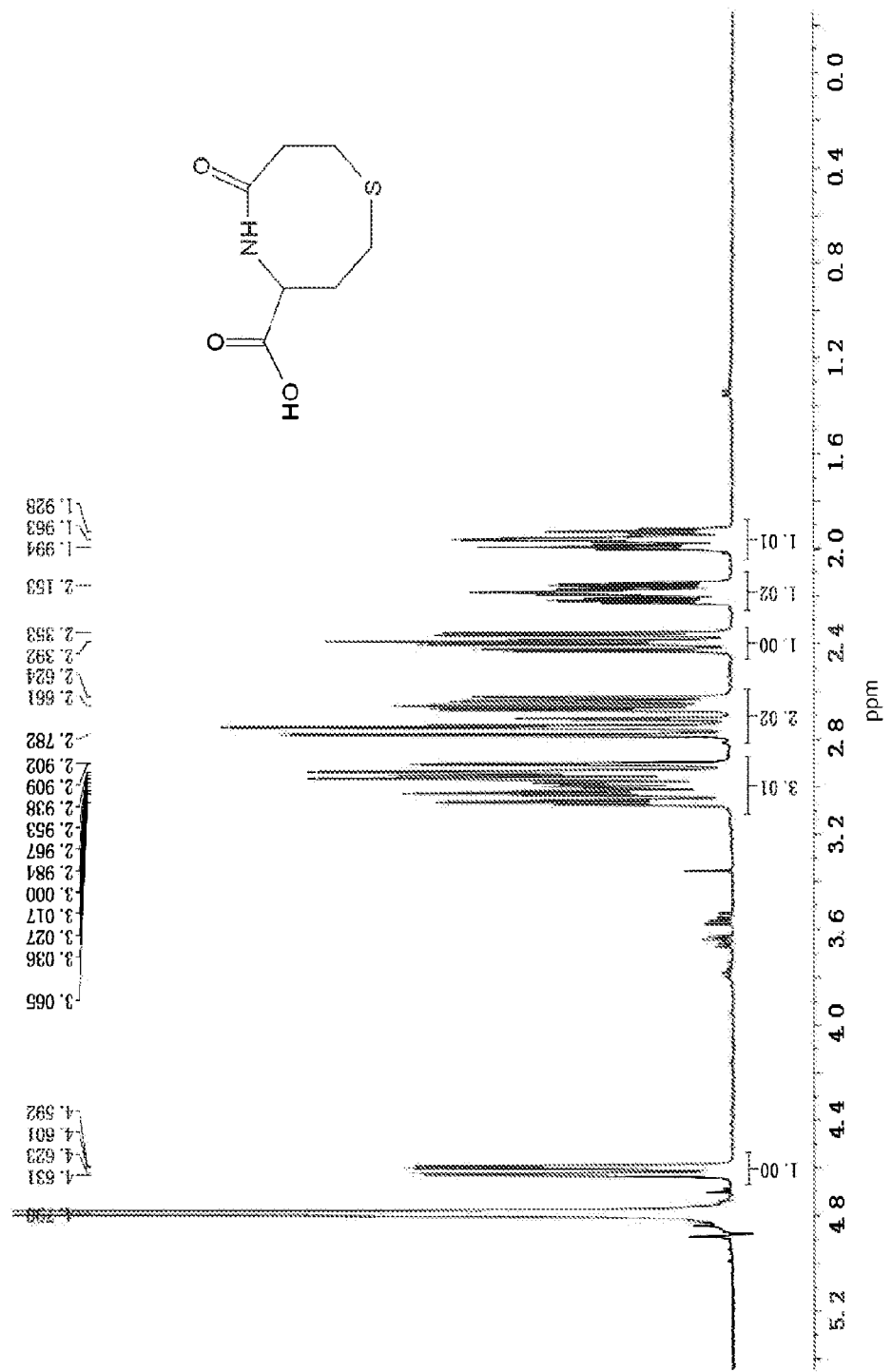
FIG. 26 is a $^1$H NMR (400 MHz) spectrum of compound 3b in D$_2$O.
Figure 27:
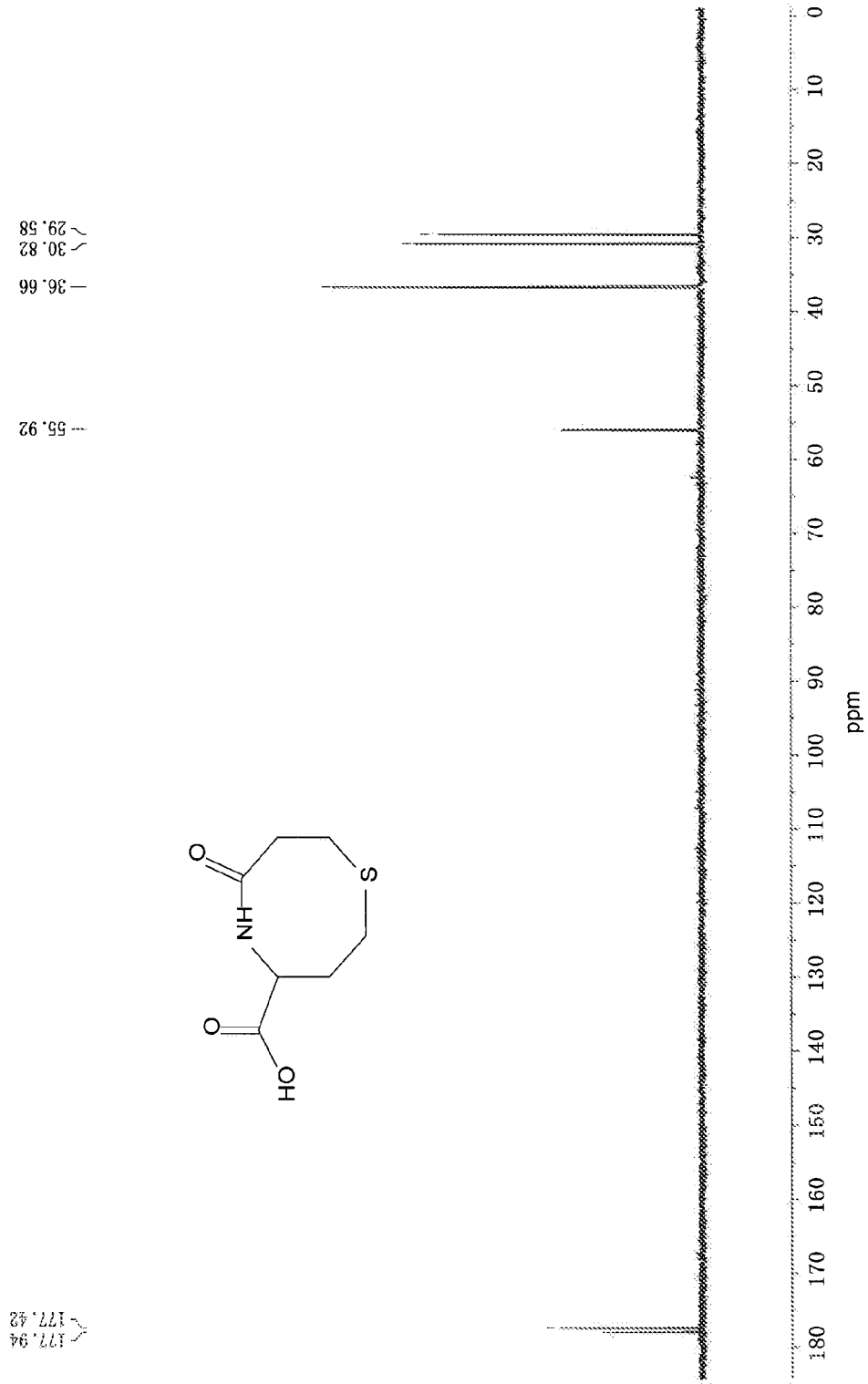
FIG. 27 is a $^{13}$C NMR (100 MHz) spectrum of compound 3b in D$_2$O.

Spectroscopy confirmed the reaction mechanism. Formation of HMBT was demonstrated by comparison of the product's $^1$H NMR data with that of authentic HMBT (FIG. 21). FIG. 22 is a comparison of the fluorescence spectra ($\lambda_{ex}$=304 nm) of probe 4 and HMBT (both 10 μM) in EtOH:phosphate buffer (20 mM, pH 7.4, 2:8 v/v). The formation of compounds 3a and 3b was confirmed by $^1$H NMR, $^{13}$C NMR, $^1$H-$^{13}$C COSY NMR and high-resolution mass spectroscopy (HRMS) (FIGS. 23-29). The spectra clearly demonstrated that an intramolecular cyclization is involved in the selective signaling event.

3a: $^1$H NMR (CDCl$_3$, 400 MHz), δ (ppm) (FIG. 23): 4.34 (dd, 1H, $J_1$=2.0 Hz, $J_2$=9.2 Hz), 3.10-3.00 (m, 2H), 2.93-2.75 (m, 4H). $^{13}$C NMR (CDCl$_3$, 100 MHz) (FIG. 24), δ 178.64, 175.17, 59.92, 39.61, 33.67, 135.53, 23.03. ESI-FTMS (FIG. 25) m/z=174.0228 [M–H]$^-$, calc. 174.0225 for $C_6H_8NO_3S$.

Figure 28:
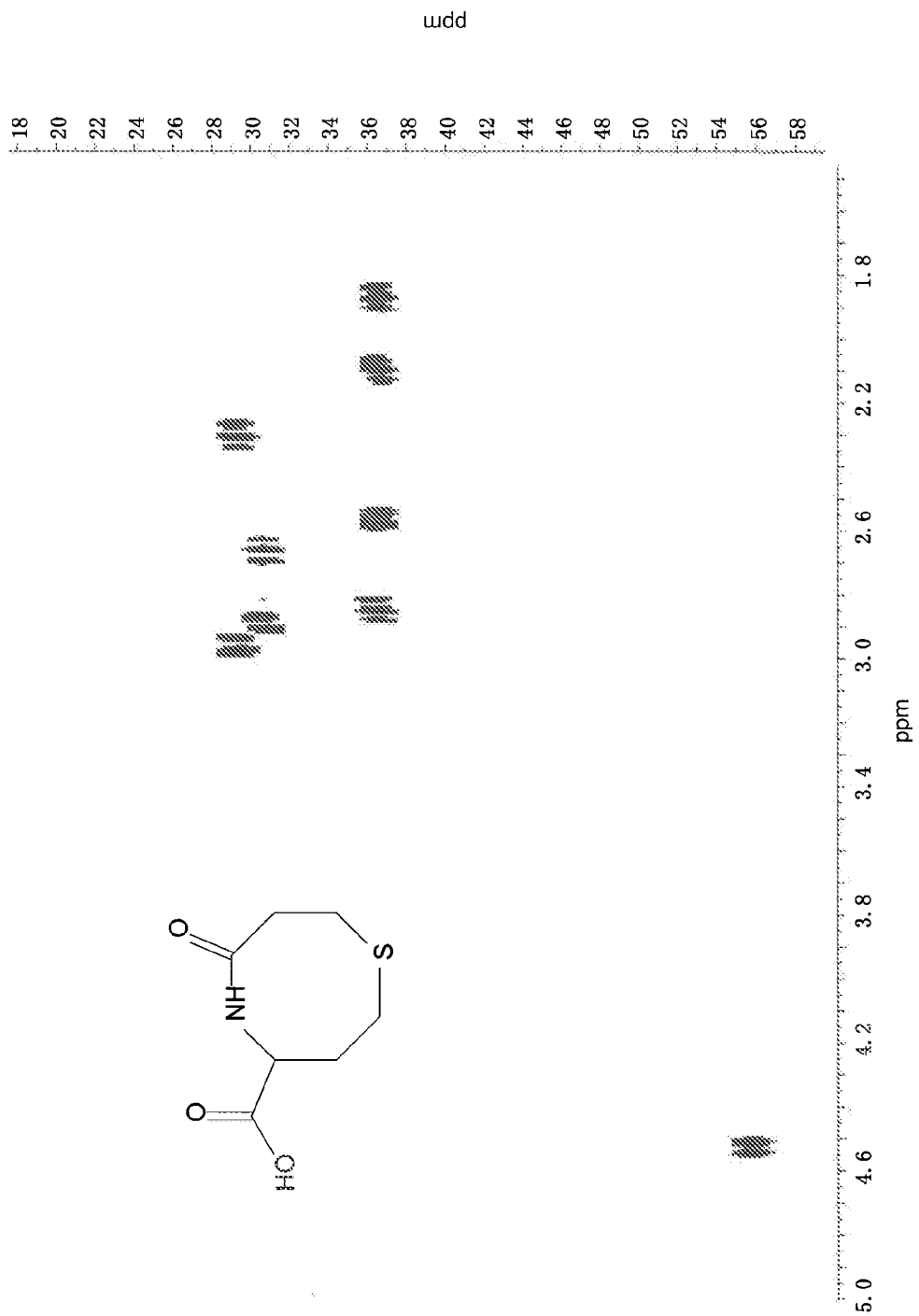
FIG. 28 is a $^1$H-$^{13}$C COSY NMR spectrum of 3b.
Figure 29:
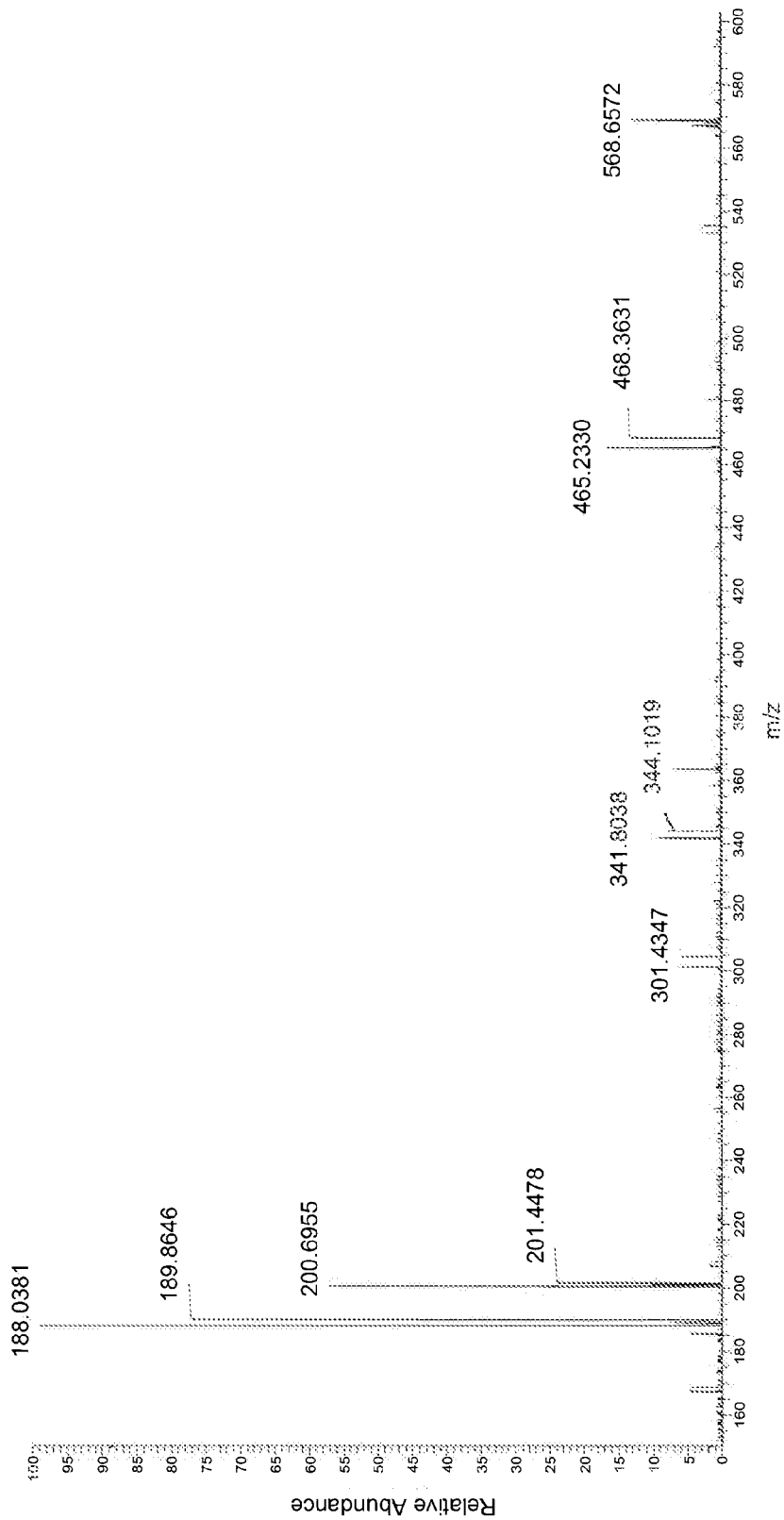
FIG. 29 is a high-resolution mass spectrum of compound 3b (6-n_110419180301 #8-13; RT: 0.12-0.20; AV: 6; NL: 1.32E4; T: FTMS−p ESI Full ms [150.00-600.00]).

3b: $^1$H NMR (D$_2$O, 400 MHz), δ (ppm) (FIG. 26): 4.61 (dd, 1H, $J_1$=3.6 Hz, $J_2$=12.4 Hz), 3.07-2.90 (m, 3H), 2.78-2.62 (m, 2H), 2.43-2.35 (m, 1H), 2.23-2.14 (m, 1H), 1.96 (t, 1H, J=12 Hz). $^{13}$C NMR (CDCl$_3$, 100 MHz) (FIG. 27), δ 177.94, 177.42, 55.92, 36.66, 30.82, 29.85. From its structure, compound 3b is predicted to have 7 peaks in its $^{13}$C spectrum. However, only 6 peaks were observed. The peak at 36.66 can be attributed to two overlapping carbons. A $^1$H-$^{13}$C COSY NMR spectrum of 3b confirmed this analysis (FIG. 28). ESI-FTMS (FIG. 29) m/z=188.0381 [M–H]$^-$, calc. 188.0381 for $C_7H_{10}NO_3S$.

Figure 30:
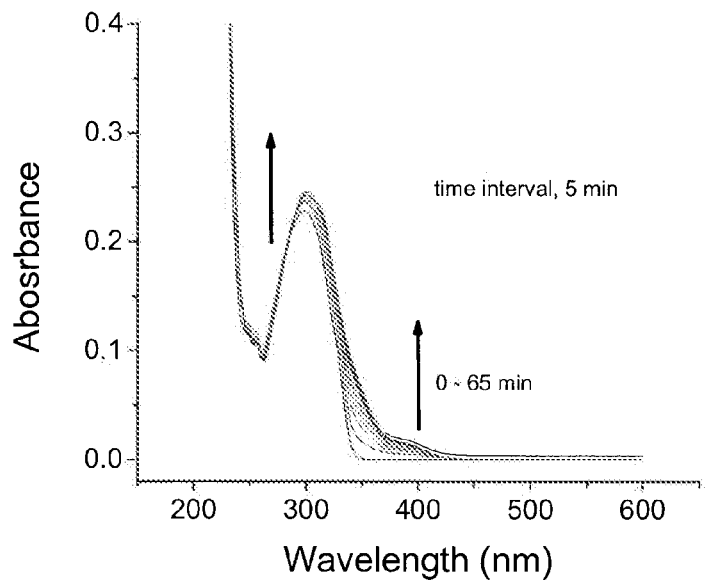
FIG. 30 is a graph of absorbance versus wavelength illustrating the time-dependent UV-visible spectral changes of probe 4 (20 μM) with Cys (1 equiv) in EtOH:phosphate buffer (20 mM, pH 7.4, 2:8 v/v).

The fluorescence sensing behavior of probe 4 toward Cys was investigated using a 20 μM solution of probe 4 in EtOH:H$_2$O (2:8, v/v) solution buffered at pH 7.4 (phosphate buffer, 0.01 M). Upon addition of Cys (1 equiv), the emission at 377 nm increased initially (FIG. 2). As the reaction progressed, the emission band at 377 nm successively decreased with concomitant growth of the keto band at 487 nm (FIGS. 3A-B, and a well-defined isoemissive point appeared at 427 nm (FIG. 4). FIG. 30 depicts the UV-visible spectral changes as the reaction progressed over 65 minutes.

Figure 31A:
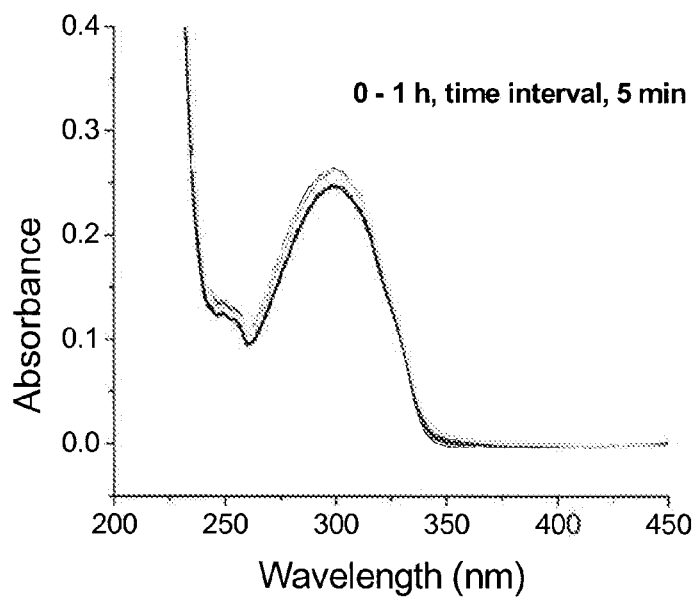
FIGS. 31A and 31B are graphs of absorbance versus wavelength illustrating the time-dependent UV-visible spectral changes of probe 4 (20 μM) with Hcy (1 equiv) in EtOH:phosphate buffer (20 mM, pH 7.4, 2:8 v/v); 0-1 h (FIG. 31A); 75 min-15 h (FIG. 31B).
Figure 31B:
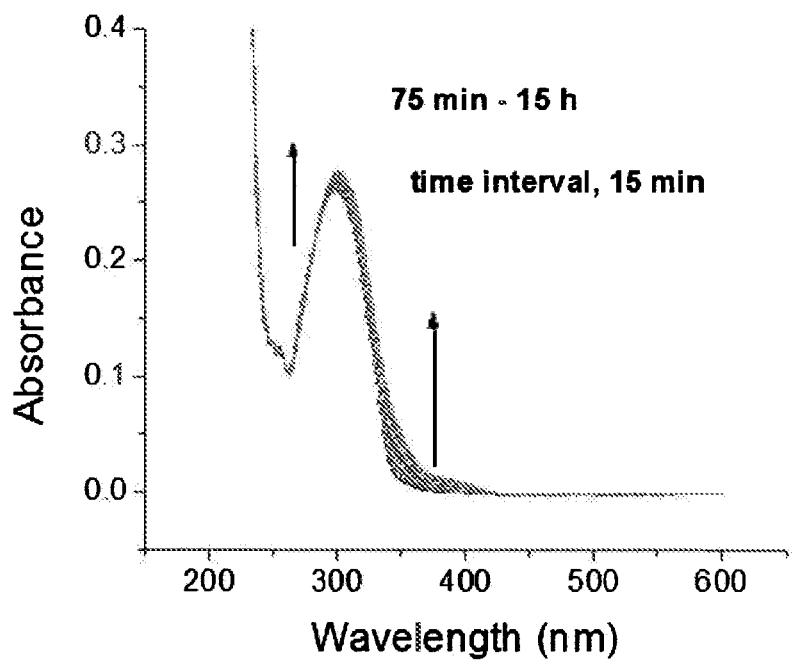

In the case of Hcy, emission at 377 nm steadily increased over time for 55 minutes (FIG. 5), followed by a decrease in emission at 377 nm after 55 minutes accompanied by an increase of the emission at 487 nm (FIG. 6, FIGS. 7A-B). FIGS. 31A-B depict the UV-visible spectral changes as the reaction progressed over 65 minutes.

Example 3

Probe 4 Selectivity Characterization

Figure 32:
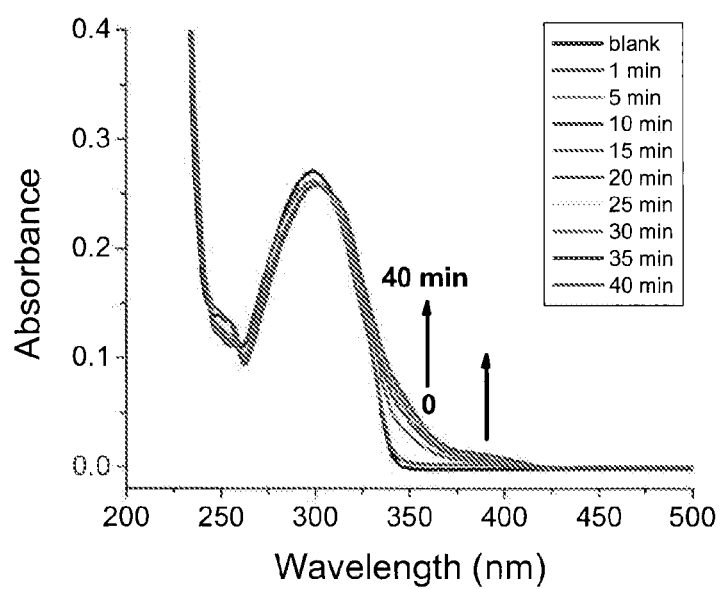
FIG. 32 is a graph of absorbance versus wavelength illustrating the time-dependent UV-visible spectral changes of probe 4 (20 μM) with cysteamine (20 μM) in EtOH:phosphate buffer (20 mM, pH 7.4, 2:8 v/v).

Control experiments were carried out to prove that the amino group of Cys was needed in the selective cyclization reaction. First, cysteamine (1 equivalent) was combined with probe 4 (20 µM) in ethanol:phosphate buffer (20 mM, pH 7.4, 2.8 v/v). Fluorescence was evaluated over time using an excitation wavelength of 304 nm. Similar fluorescence changes were observed as for Cys under analogous reaction conditions (FIGS. 8A-D). FIG. 32 depicts the UV-visible spectral changes as the reaction progressed over 40 minutes.

Figure 33:
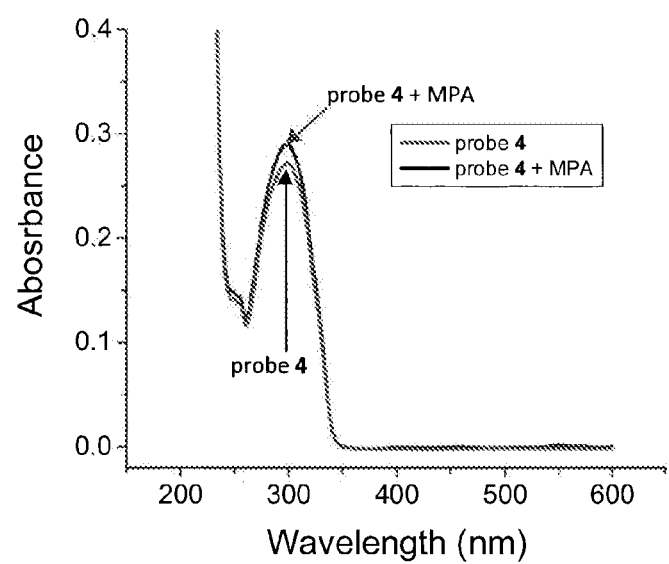
FIG. 33 is a graph of absorbance versus wavelength illustrating the UV-visible spectra of probe 4 (20 μM) in the presence and absence of 3-mercaptopropanoic acid (91.2 μM) in EtOH:phosphate buffer (20 mM, pH 7.4, 2:8 v/v). Reaction time, 1 h.

Next, 3-mercaptopropanoic acid (MPA, 91.2 µM) was combined with probe 4 in ethanol:phosphate buffer (20 mM, pH 7.4, 2.8 v/v). Fluorescence was evaluated over time using an excitation wavelength of 304 nm (FIG. 9). MPA exhibited fluorescence emission centered at 377 nm, demonstrating that only the conjugate addition product formed. FIG. 33 depicts the UV-visible spectra of probe 4 in the presence and absence of MPA after 1 hour.

Figure 34:
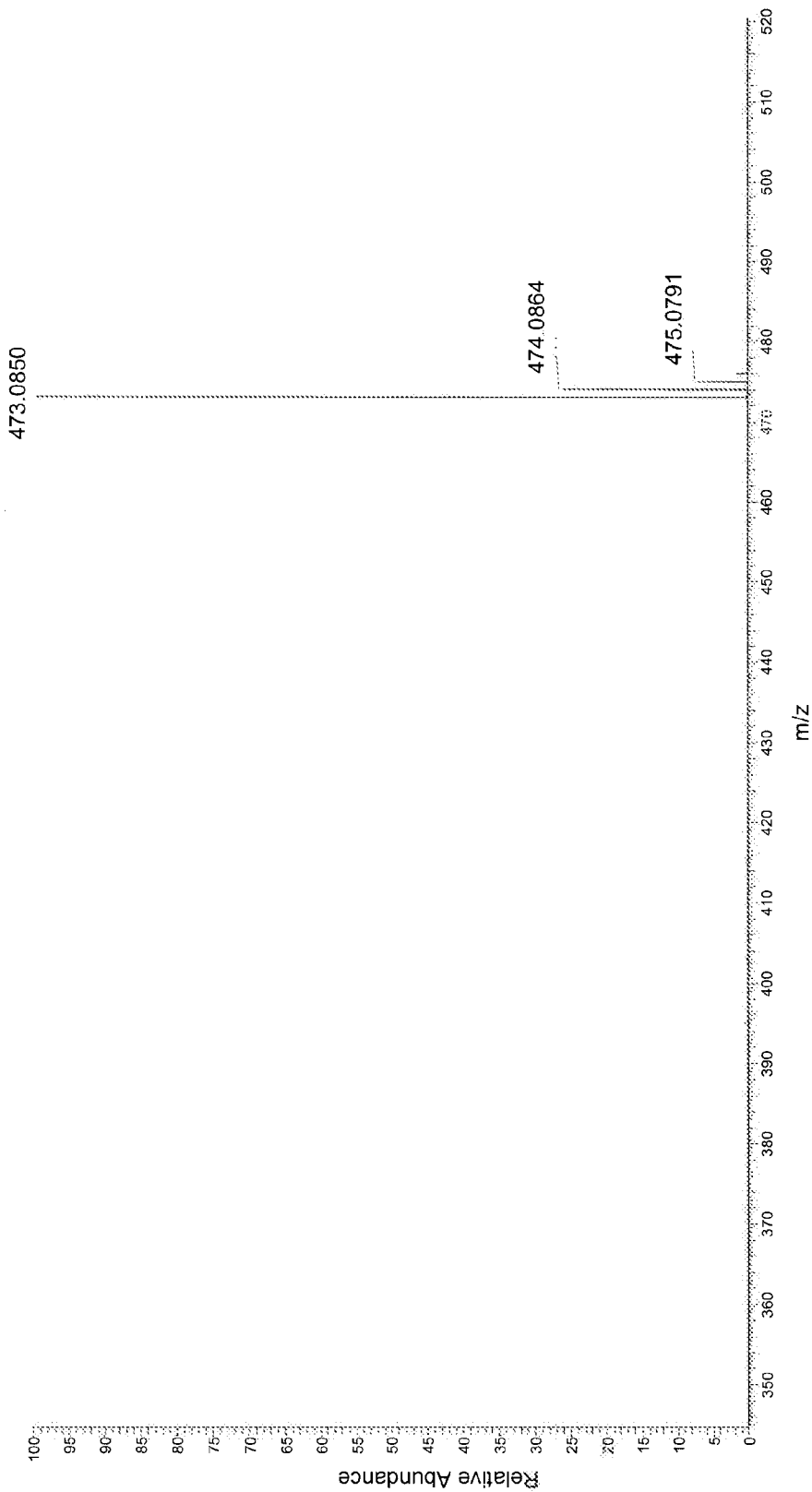
FIG. 34 is a high-resolution mass spectrum of the conjugate addition adduct of probe 4 with N-acetyl-L-cysteine (9-n2 110419190801 #1-20; RT: 0.01-0.31; AV: 20; NL: 1.66E6; T: FTMS−p ESI Full ms [200.00-600.00]).

N-acetyl-L-cysteine (NAC, 20 µM) was combined with probe 4 in ethanol:phosphate buffer (20 mM, pH 7.4, 2.8 v/v). Fluorescence was evaluated over time using an excitation wavelength of 304 nm (FIG. 10). NAC produced a similar result to that of MPA, i.e., formation of the conjugate addition adduct. The latter product was evidenced via HRMS data (ESI-FTMS m/z=473.0850 [M−H]⁻, calc. 473.0841 for $C_{22}H_{21}N_2O_6S_2$, FIG. 34).

Probe selectivity for Cys and Hcy was demonstrated by evaluating changes in fluorescence intensity of 4 caused by other analytes, such as leucine, proline, arginine, histidine, valine, methionine, threonine, glutamine, alanine, aspartic acid, norleucine, isoleucine, lysine, cystine and homocystine. Each analyte (10 µM) was combined with probe 4 (20 µM) in ethanol:phosphate buffer (20 mM, pH 7.4, 2.8 v/v). Fluorescence was evaluated after 40 minutes using an excitation wavelength of 304 nm. As shown in FIG. 11, only Cys and Hcy exhibited significant fluorescence intensity changes at 487 and 377 nm, respectively, while other amino acids caused no fluorescence intensity changes under the same conditions.

Figure 12:
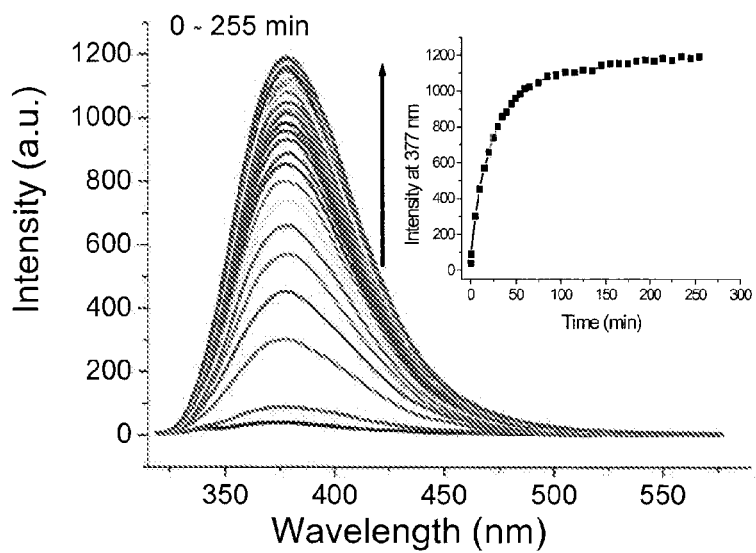
FIG. 12 is a graph of absorbance intensity versus wavelength illustrating the time-dependent fluorescence spectral changes of probe 4 (20 μM) with GSH (1 equiv) in EtOH:phosphate buffer (20 mM, pH 7.4, 2:8 v/v). $\lambda_{ex}$=304 nm. Inset: Time-dependent fluorescence intensity changes at 377 nm.
Figure 35:
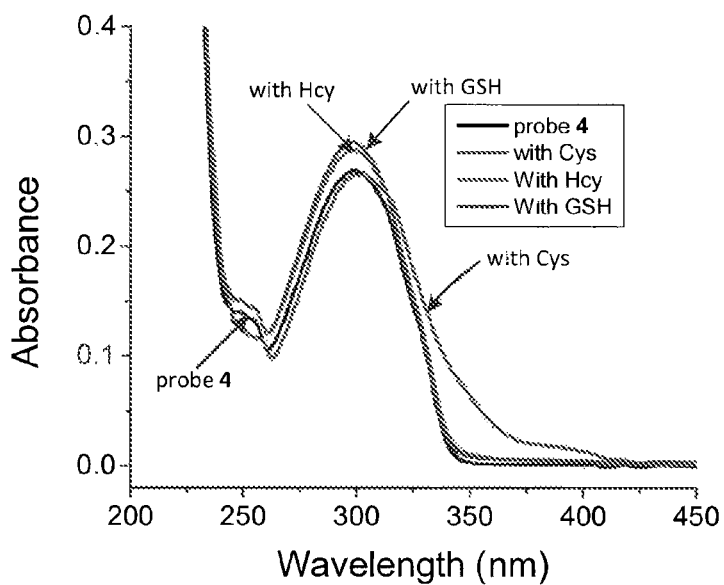
FIG. 35 is a graph of absorbance versus wavelength illustrating the UV-visible spectra of probe 4 (20 μM) in the presence of different biothiols (1 equiv) in EtOH:phosphate buffer (20 mM, pH 7.4, 2:8 v/v). Reaction time, 40 min.

Glutathione (GSH), however, was discovered to produce enol-like emission at 377 nm. GSH (1 equivalent) was combined with probe 4 in ethanol:phosphate buffer (20 mM, pH 7.4, 2.8 v/v). Fluorescence was evaluated over 255 minutes using an excitation wavelength of 304 nm (FIG. 12). As shown in FIG. 12, fluorescence at 377 nm increased for more than 50 minutes before leveling off. FIG. 35 depicts the UV-visible spectra of probe 4 in the presence Cys, Hcy, and GSH after 40 minutes.

Figure 13:
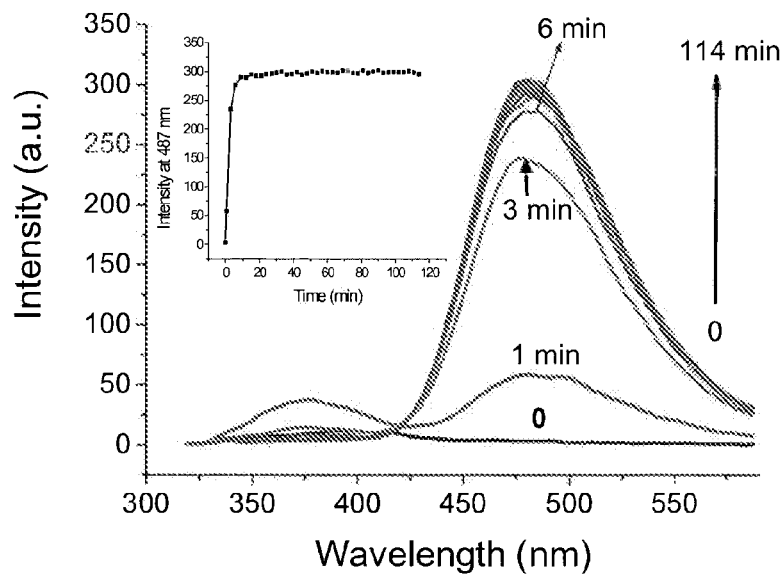
FIG. 13 is a graph of absorbance intensity versus wavelength illustrating the time-dependent fluorescence spectral changes of probe 4 (10 μM) with Cys (2 equiv) in CTAB media (1.0 mM) buffered at 7.4 (phosphate buffer, 20 mM). $\lambda_{ex}$=304 nm. Inset: time-dependent fluorescence intensity changes at 487 nm.
Figure 14:
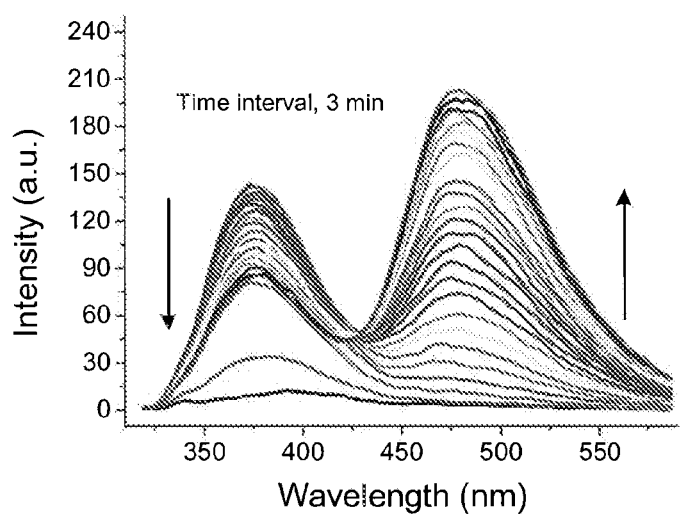
FIG. 14 is a graph of absorbance intensity versus wavelength illustrating the time-dependent fluorescence spectral changes of probe 4 (10 μM) with Hcy (2 equiv) in CTAB media (1.0 mM) buffered at 7.4 (phosphate buffer, 20 mM) over a time period of 0-75 minutes. $\lambda_{ex}$=304 nm.

Analogous cyclocondensation reactions of aminothiols are catalyzed by surfactants (Sharma et al., *Tetrahedron Lett.* 2008, 49, 4269-4271). Thus, a surfactant-containing media was prepared with 10 mM cetyltrimethylammonium bromide (CTAB) buffered to pH 7.4 in phosphate buffer (20 mM). Reaction of Cys (2 equivalents) in the CTAB media was evaluated over 114 minutes. Fluorescence intensity at 487 nm rapidly increased, and was complete within 9 minutes (FIG. 13). Reaction of Hcy (2 equivalents) in the CTAB media was evaluated over 75 minutes. As shown in FIGS. 14 and 15, fluorescence intensity at 377 nm initially increased for about 15 minutes, and then decreased; fluorescence intensity at 487 nm slowly increased over time in a linear fashion. Reaction of GSH (2 equivalents) in the CTAB media was evaluated over 6 minutes (FIG. 16). Fluorescence intensity at 377 nm increased very rapidly and began to level off after 3 minutes. The reaction appeared to be complete after about 5 minutes. No significant fluorescence at 487 nm was evident.

FIG. 17 demonstrates that Cys and Hcy can be differentiated by their emission at 487 nm in CTAB media. Fluorescence emission from Cys reached a maximum within 9 minutes and levels off. In contrast, very little fluorescence emission from Hcy was seen at 9 minutes, and emission continued to increase over a reaction time of 75 minutes.

Example 4

Simultaneous Determination of Cysteine and Homocysteine

Figure 36:
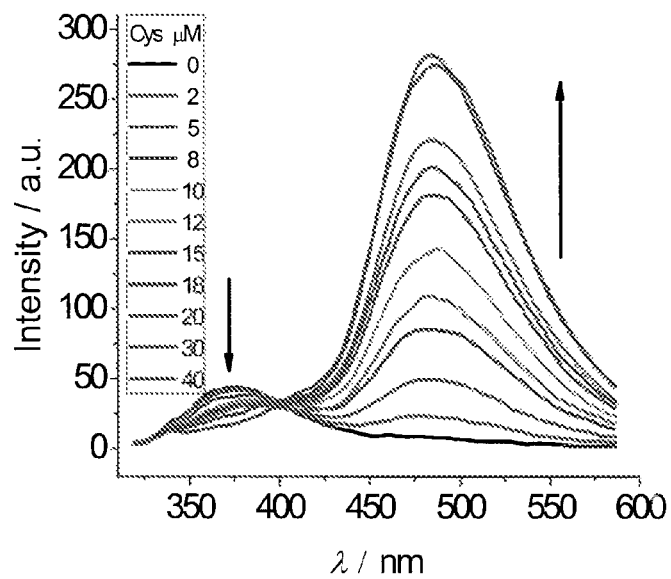
FIG. 36 is a graph of fluorescence intensity versus wavelength for the reaction of probe 4 with varying concentrations of cysteine. $\lambda_{ex}$=304 nm.
Figure 37:
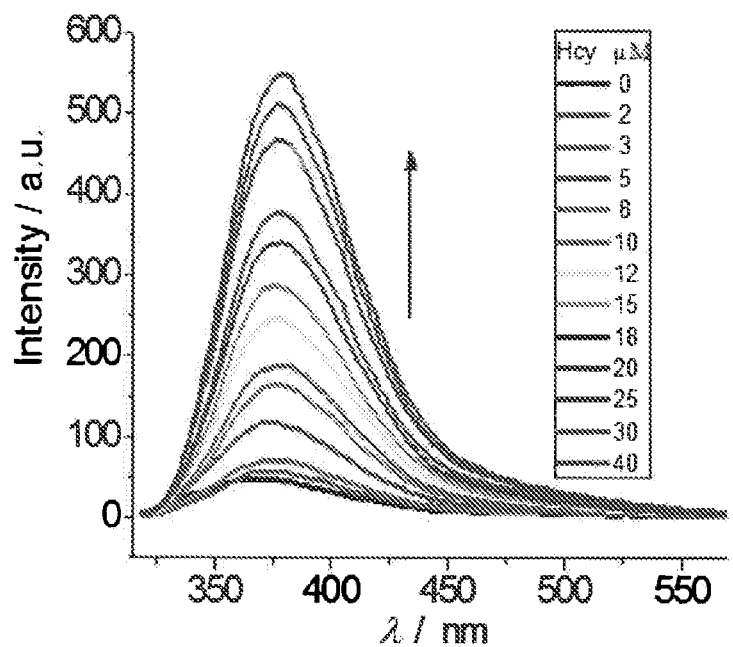
FIG. 37 is a graph of fluorescence intensity versus wavelength for the reaction of probe 4 with varying concentrations of homocysteine. $\lambda_{ex}$=304 nm.
Figure 38A:
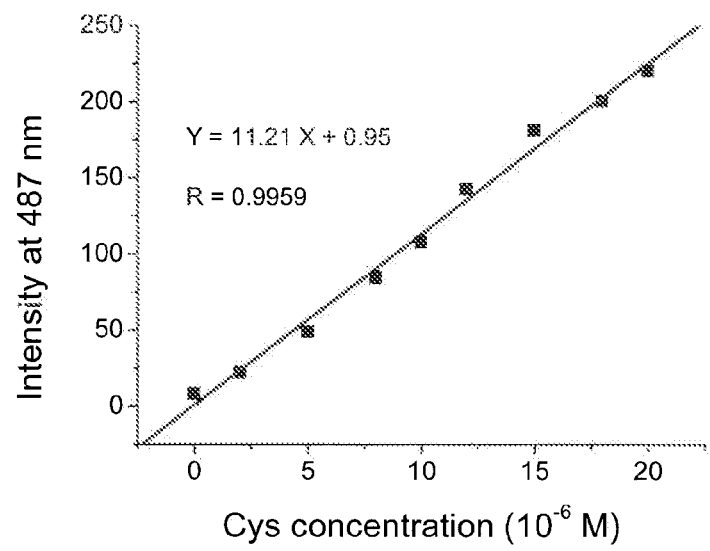
FIG. 38A is a graph of fluorescence intensity at 487 nm versus cysteine concentration for a reaction of probe 4 with cysteine.
Figure 38B:
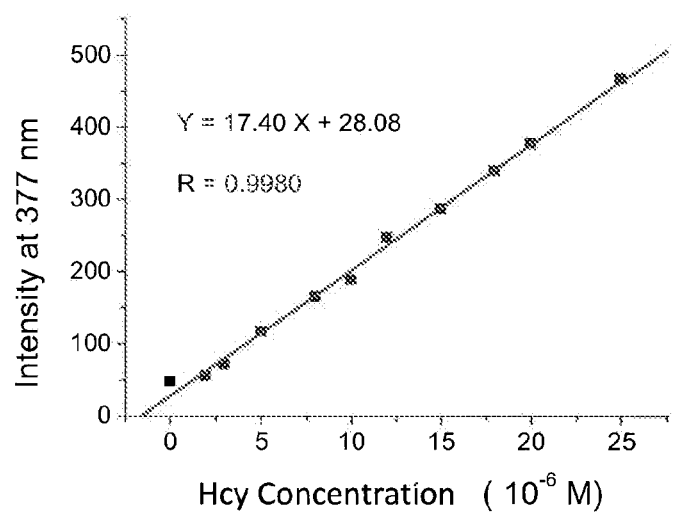
FIG. 38B is a graph of fluorescence intensity at 377 nm versus homocysteine concentration for a reaction of probe 4 with homocysteine.
Figure 39:
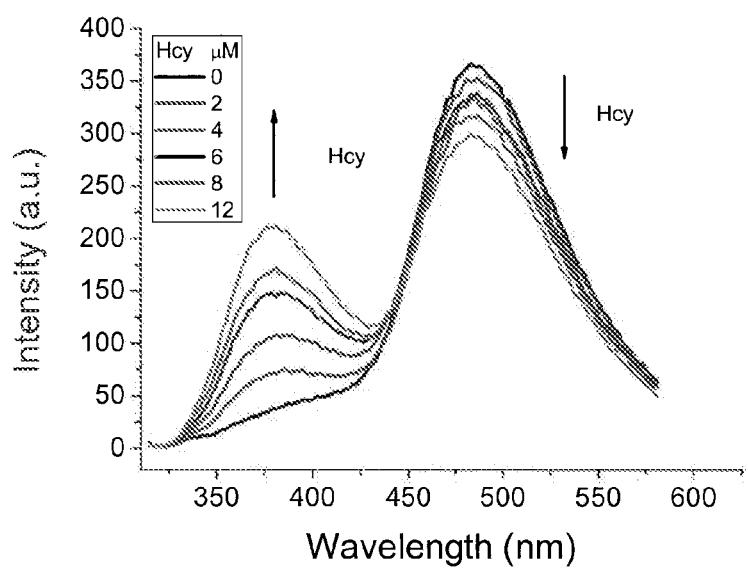
FIG. 39 is a graph of fluorescence intensity versus wavelength illustrating the fluorescence spectra ($\lambda_{ex}$=304 nm) of probe 4 (50 μM) in the presence of cysteine (40 μM) and different concentrations of homocysteine (0-12 µM) in EtOH: phosphate buffer (20 mM, pH 7.4, 2:8 v/v), reaction time 40 minutes.
Figure 40:
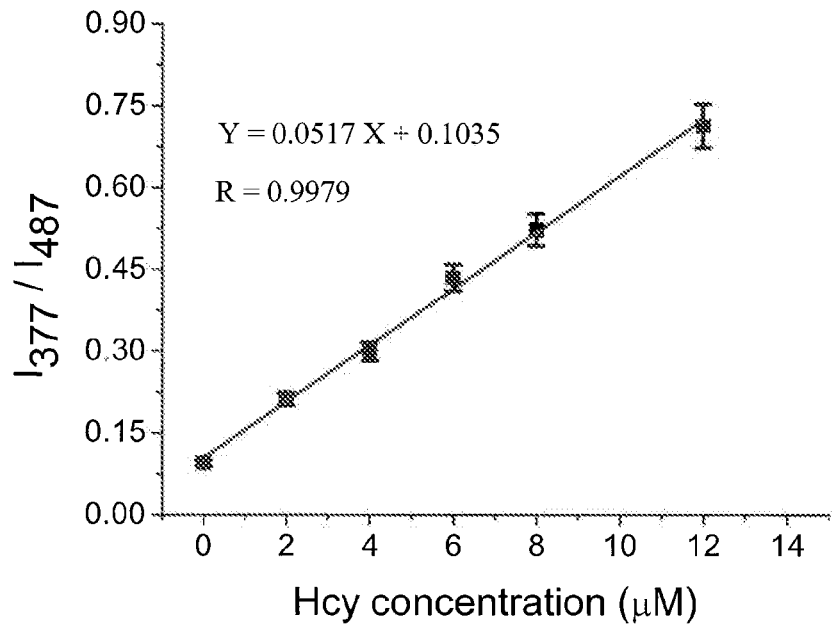
FIG. 40 is a graph demonstrating the ratiometric (dual wavelength) response of homocycsteine concentration derived from the data in FIG. 39.
Figure 41:
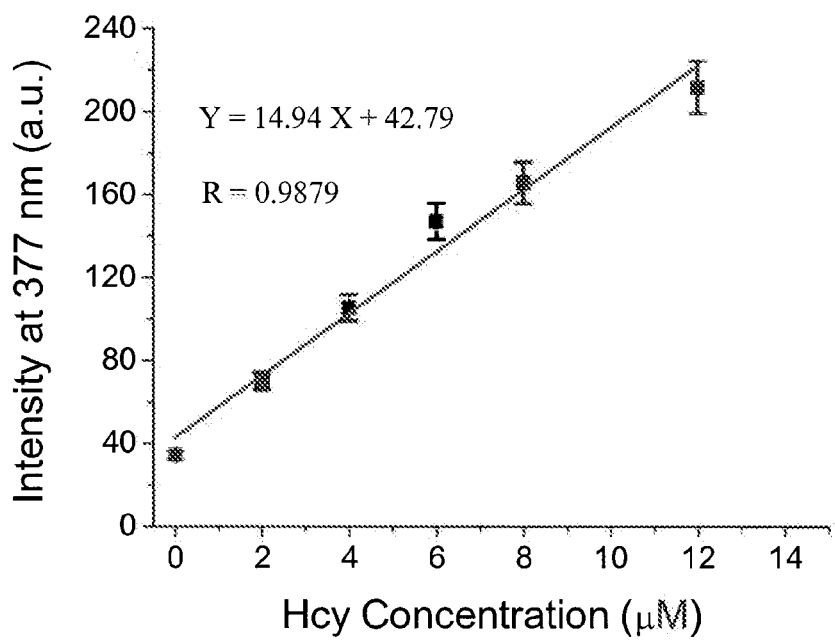
FIG. 41 is a graph of fluorescence intensity of probe 4 at 377 nm versus homocysteine concentration derived from the data in FIG. 39.

The kinetic differences in the intramolecular cyclization reactions of 5a and 5b (Scheme 2) observed in Example 3, indicated that Cys and Hcy could be simultaneously determined over a time course. Cys and Hcy were combined separately with probe 4 in EtOH:phosphate buffer (0.01 M, pH 7.4) (2:8, v/v), and fluorescence was measured over 40 minutes. As shown in FIGS. 36 and 37, fluorescence intensity at 487 nm increased with increasing Cys concentration (FIB. 36) and fluorescence intensity at 377 nm increased with increasing Hcy concentration (FIG. 37). The fluorescent intensity was linearly proportional to the amount of Cys from 0 to 20 µM (FIG. 38A) and 0 to 25 µM for Hcy (FIG. 38B). The detection limits of Cys and Hcy are 0.11 µM and 0.18 µM, respectively, which is below the requisite detection limits for Cys and Hcy assays in human plasma samples. The assay can distinguish concentration changes on the order of 2-3 µM. Such Cysteine and homocysteine were determined simultaneously in a single solution. A solution including Cys (40 µM) and Hcy (0-12 µM) was added to a solution of probe 4 (50 µM) in ethanol:phosphate buffer (20 mM, pH 7.4, 2:8 v/v) at ambient temperature. Fluorescence intensity ($\lambda_{ex}$=304 nm) was measured 40 minutes after the solutions were combined. As shown in FIG. 39, Hcy was detectable at 377 nm with no significant interference from a physiological concentration of cysteine. As expected fluorescence intensity at 377 nm increased as the concentration of Hcy increased. The ratio of fluorescence intensity at 377 nm to fluorescence intensity at 487 nm increased linearly as Hcy concentration increased (FIG. 40). FIG. 41 demonstrates that fluorescence intensity at 377 nm increased linearly as Hcy concentration increased.

Figure 42:
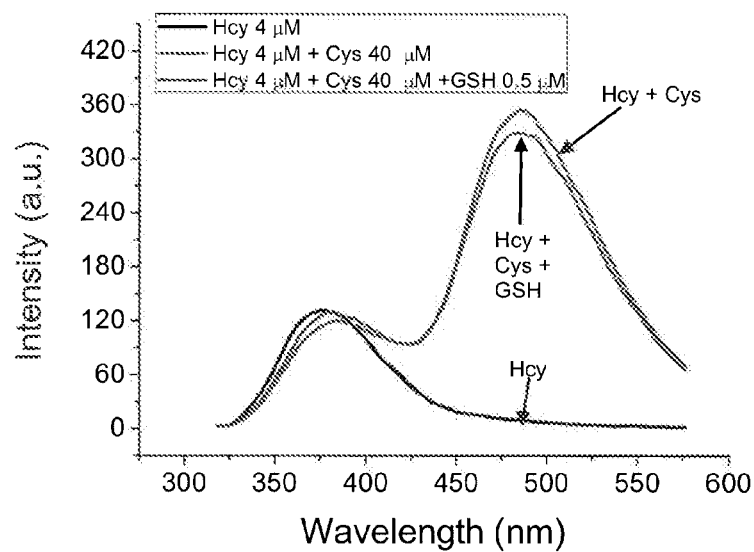
FIG. 42 is a graph of fluorescence intensity versus wavelength illustrating the fluorescence spectra ($\lambda_{ex}$=304 nm) of probe 4 (50 µM) in the presence of 1) homocysteine (4 µM), 2) homocysteine (4 µM) and cysteine (40 µM), and 3) homocysteine (4 µM), cysteine (40 µM), and glutathione (0.5 µM) in EtOH:phosphate buffer (20 mM, pH 7.4, 2:8 v/v), reaction time 40 minutes.

Homocysteine also can be determined in the presence of both cysteine and glutathione. Solutions of 1) Hcy (4 µM), 2) Hcy (4 µM) and Cys (40 µM), or 3) Hcy (4 µM), Cys (40 µM), and GSH (0.5 µM) were combined with probe 4 (50 µM) in ethanol:phosphate buffer (20 mM, pH 7.4, 2:8 v/v) at ambient temperature. Fluorescence intensity ($\lambda_{ex}$=304 nm) was measured 40 minutes after the solutions were combined. FIG. 42 demonstrates that Hcy was detectable with no significant interference from physiological concentrations (i.e., plasma level concentrations) of glutathione, providing further evidence that probe 4 has potential utility in clinical diagnosis.

Example 5

Simultaneous Determination of Cysteine and Homocysteine in Deproteinized Human Plasma Further evaluation demonstrated that cysteine can be detected in deproteinized human plasma using probe 4. Cysteine and homocysteine also were detected simultaneously in deproteinized human plasma with probe 4.

Figure 43:
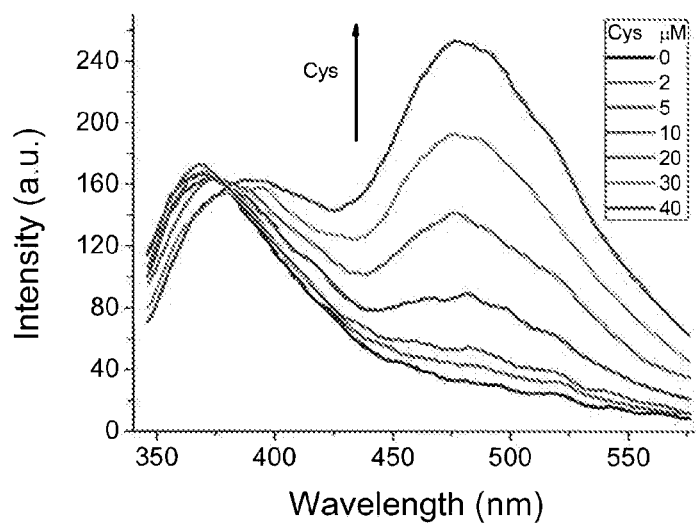
FIG. 43 is a graph of fluorescence intensity versus wavelength illustration the fluorescence spectra ($\lambda_{ex}$=330 nm) of probe 4 (50 µM) in the presence of varying concentrations of cysteine (0-40 µM) in 10% deproteinized human plasma diluted in EtOH:phosphate buffer (20 mM, pH 7.4, 2:8 v/v), reaction time 40 minutes.
Figure 44:
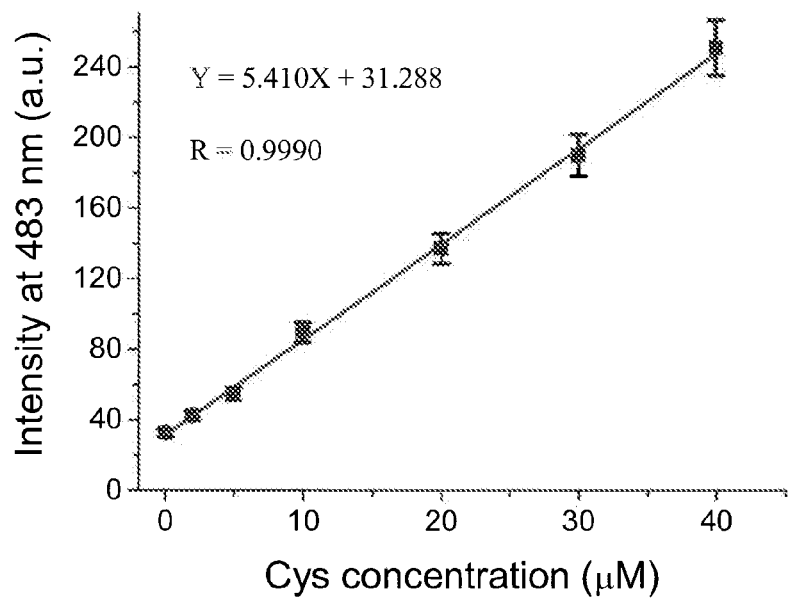
FIG. 44 is a graph of fluorescence intensity at 483 nm versus cysteine concentration derived from the data in FIG. 43.

Probe 4 (50 μM) was combined with cysteine (0-40 μM) in 10% deproteinized human plasma diluted in ethanol:phosphate buffer (20 mM, pH 7.4, 2:8 v/v) at ambient temperature. Fluorescence intensity ($\lambda_{ex}$=330 nm) was measured 40 minutes after the solutions were combined. To reduce the background fluorescence from human plasma, the excitation wavelength was selected at 330 nm instead of maximum excitation wavelength 304 nm. FIG. 43 demonstrates that fluorescence intensity at 475-500 nm increased as Cys concentration increased. Fluorescence intensity at 483 nm increased linearly as Cys concentration increased (FIG. 44), with reaction times similar to those observed in buffer.

Figure 45:
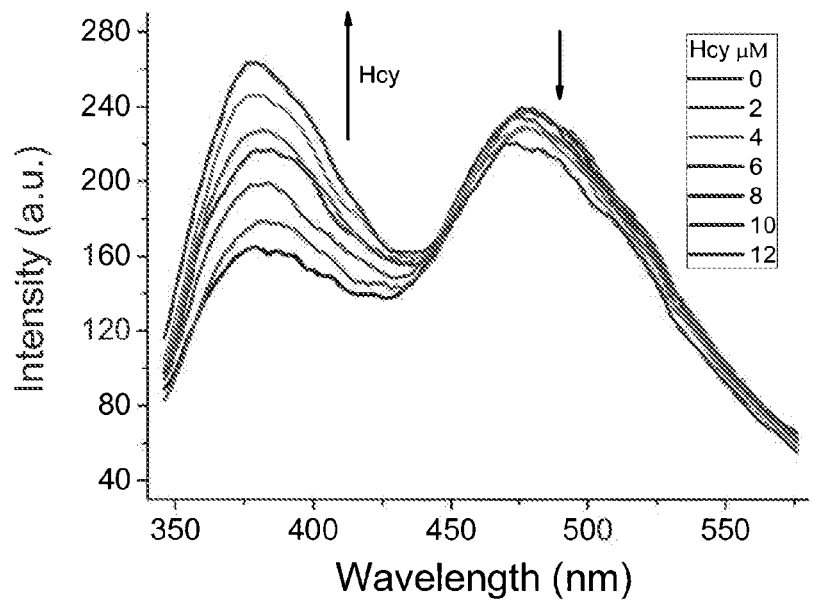
FIG. 45 is a graph of fluorescence intensity versus wavelength illustration the fluorescence spectra ($\lambda_{ex}$=330 nm) of probe 4 (50 µM) in the presence of varying concentrations of homocysteine (0-12 µM) and cysteine (40 µM) in 10% deproteinized human plasma diluted in EtOH:phosphate buffer (20 mM, pH 7.4, 2:8 v/v), reaction time 40 minutes.
Figure 46:
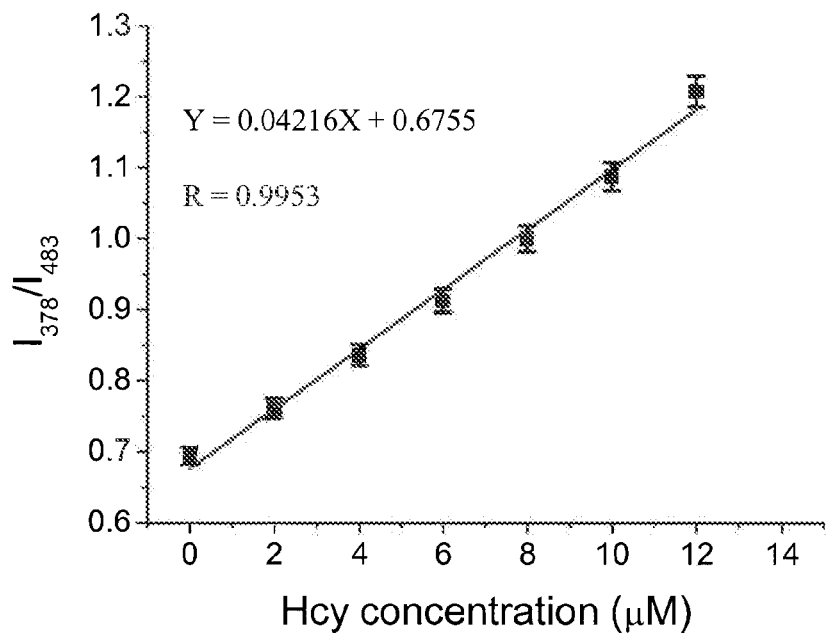
FIG. 46 is a graph demonstrating the ratiometric (dual wavelength) response of homocycsteine concentration in the presence of excess cysteine and 10% deproteinized human plasma (derived from the data in FIG. 45).
Figure 47:
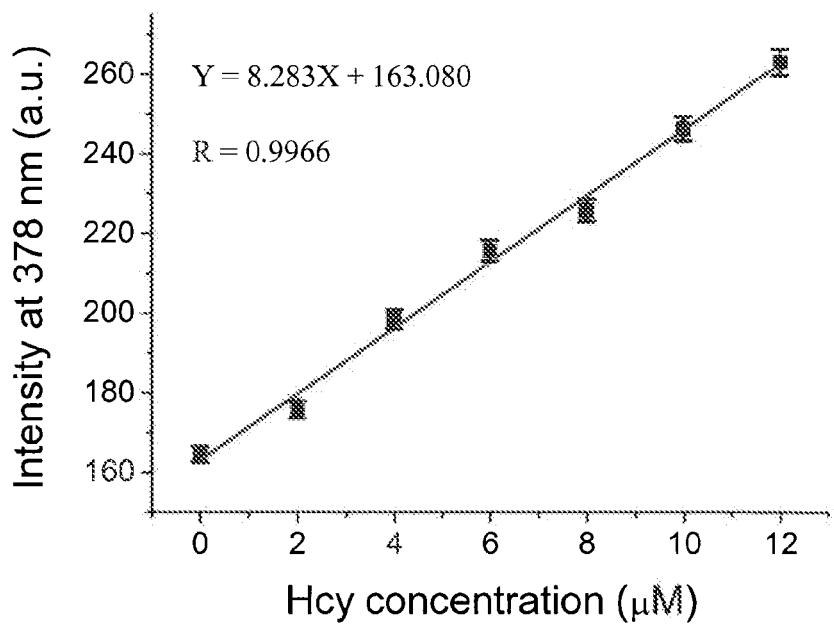
FIG. 47 is a graph of fluorescence intensity of probe 4 at 378 nm versus homocysteine concentration derived from the data in FIG. 45.

Next, probe 4 (50 μM) was combined with Hcy (0-12 μM) and Cys (40 μM) in 10% deproteinized human plasma diluted in ethanol:phosphate buffer (20 mM, pH 7.4, 2:8 v/v) at ambient temperature. Fluorescence intensity ($\lambda_{ex}$=330 nm) was measured 40 minutes after the solutions were combined. As shown in FIG. 45, fluorescence intensity at 375-380 nm increased as Hcy concentration increased. The ratio of fluorescence intensity at 378 nm to fluorescence intensity at 483 nm increased linearly as Hcy concentration increased (FIG. 46). FIG. 47 demonstrates that fluorescence intensity at 378 nm increased linearly as Hcy concentration increased. Moreover, the fluorescence increase at 378 nm can be observed for Hcy even in the presence of excess Cys.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for detecting at least one compound comprising a thiol group and an amino group, comprising:
    combining a sample potentially comprising at least one compound comprising a thiol group and an amino group with a solution comprising a probe having a structure according to general formula II

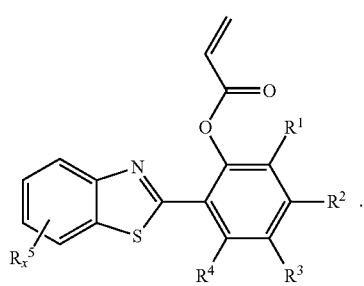

(II)

where $R^1$-$R^4$ independently are hydrogen, hydroxyl, halogen, thiol, thioether, lower aliphatic, or lower alkoxy, x is an integer from 0 to 4, and each $R^5$ independently is halogen, hydroxyl, thiol, thioether, lower aliphatic, or lower alkoxy;
    allowing a reaction between the compound and the probe to proceed for an effective period of time; and
    detecting the at least one compound by detecting fluorescence of the solution.

2. The method of claim 1 where the at least one compound is cysteine, homocysteine, or a combination thereof.

3. The method of claim 1 where detecting fluorescence of the solution comprises:
    obtaining a fluorescence spectrum after the effective period of time; or
    monitoring a fluorescence spectrum of the solution over a period of time ranging from zero minutes to a time greater than or equal to the effective period of time.

4. The method of claim 1 where $R^1$ is methoxy, $R^2$-$R^4$ are hydrogen, and x is 0.

5. The method of claim 4 where detecting fluorescence of the solution comprises detecting the fluorescence at 377 nm, at 487 nm, or at 377 nm and 487 nm after the effective period of time or over a period of time ranging from zero minutes to the effective period of time.

6. The method of claim 4 where the at least one compound is cysteine and detecting the at least one compound comprises detecting fluorescence of the solution at 487 nm after the effective period of time.

7. The method of claim 4 where the at least one compound is homocysteine and detecting the at least one compound comprises detecting fluorescence of the solution at 377 nm after the effective period of time.

8. The method of claim 1 where the solution further comprises a surfactant.

9. The method of claim 8 where $R^1$ is methoxy, $R^2$ is hydrogen, and x is 0.

10. The method of claim 9 where the at least one compound is cysteine, the effective period of time is 8-10 minutes, and detecting the cysteine comprises detecting fluorescence of the solution at 487 nm after the effective period of time.

11. The method of claim 9 where the at least one compound is homocysteine, the effective period of time is 8-10 minutes, and detecting the homocysteine comprises detecting fluorescence of the solution at 377 nm 8-10 minutes after combining the sample and the solution comprising the probe.

12. The method of claim 9 where the at least one compound is homocysteine, the effective period of time is 8-10 minutes, and detecting the homocysteine comprises:
    measuring fluorescence of the solution at 377 nm and 487 nm at a first time 8-10 minutes after combining the sample and the solution comprising the probe;
    measuring fluorescence of the solution at 377 nm and 487 nm at a second time after combining the sample and the solution comprising the probe, wherein the second time is greater than 8-10 minutes; and
    determining a difference in fluorescence at each of 377 nm and 487 nm at the first time and the second time, wherein a decrease in fluorescence at 377 nm and a proportional increase in fluorescence at 487 nm indicates presence of homocysteine.

13. The method of claim 9 where the at least one compound comprises cysteine, homocysteine, glutathione, one or more non-amino thiols, or a combination thereof, the effective period of time is greater than or equal to 9 minutes, and detecting the at least one compound comprises detecting fluorescence of the solution at 377 nm and 487 nm after the effective period of time.

14. The method of claim 13 further comprising identifying the at least one compound, wherein cysteine is identified based upon stable fluorescence intensity of the solution at 487 nm after 9 minutes and for a subsequent period of time of at least 5 additional minutes, glutathione and/or non-amino thiols are identified based upon stable fluorescence intensity of the solution at 377 nm after 9 minutes and for a subsequent period of time of at least 5 additional minutes, and/or homocysteine is identified based upon proportionally decreasing fluorescence intensity of the solution at 377 nm and increasing fluorescence intensity of the solution at 487 nm after 9 minutes and during a subsequent period of time of at least 5 additional minutes.

* * * * *